United States Patent
Fliri et al.

(10) Patent No.: US 6,552,015 B2
(45) Date of Patent: Apr. 22, 2003

(54) AZABICYCLOALKANE DERIVATIVES AND THERAPEUTIC USES THEREOF

(75) Inventors: Anton Franz Joseph Fliri, Stonington, CT (US); Todd William Butler, Salem, CT (US); Randall James Gallaschun, Lebanon, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/920,500

(22) Filed: Aug. 1, 2001

(65) Prior Publication Data

US 2002/0052355 A1 May 2, 2002

Related U.S. Application Data

(60) Provisional application No. 60/222,707, filed on Aug. 3, 2000.

(51) Int. Cl.[7] ............... C07D 487/08; C07D 401/06; A61K 31/505; A61P 25/00
(52) U.S. Cl. ............ 514/214.03; 514/253.04; 514/266.3; 540/582; 540/583; 540/584; 544/286; 544/362
(58) Field of Search ............... 540/582, 583, 540/584; 514/214.03, 253.04, 266.3; 544/286, 362

(56) References Cited

U.S. PATENT DOCUMENTS

| | | | |
|---|---|---|---|
| 3,726,979 A | 4/1973 | Hong | 424/250 |
| 5,296,487 A | 3/1994 | Shimazaki et al. | 514/259 |
| 5,498,610 A | 3/1996 | Chenard | 514/222.8 |

FOREIGN PATENT DOCUMENTS

| | | | |
|---|---|---|---|
| EP | 0345808 | 12/1989 | C07D/401/12 |
| EP | 0978280 | 2/2000 | C07D/453/06 |
| EP | 1083178 | 3/2001 | C07D/498/04 |
| FR | 2531709 | 2/1984 | C07D/487/04 |
| WO | WO9637494 | 11/1996 | C07D/451/02 |
| WO | WO9926478 | 6/1999 | C07D/451/02 |
| WO | WO0034284 | 6/2000 | C07D/487/08 |

OTHER PUBLICATIONS

Gilles Tamagnan et al., "N–Phthalimidoalkyl Derivatives of 2β–Carbomethoxy–3β–(4'–Iodophyl)Tropane (β–CIT): Brain Monoamine Transporter Affinity," *Bioorganic & Medicinal Chemistry Letters*, vol. 7, No. 3, pp. 337–340 (1997).

Simon M. N. Efange et al., "N–Hydroxyalkyl Derivatives of 3β–Phenyltropane and 1–Methylspiro[1H–indoline–3,4'–piperidine]: Vesamicol Analogues with Affinity for Monoamine Transporters," *J. Med. Chem.*, 40, pp. 3905–3914 (1997).

Caroline D. Cox et al., "Synthesis of Epibatidine Isomers: Reductive Heck Coupling of 2–Azabicyclo[2.2.1]hept–5–ene derivatives," *Tetrahedron*, 55 pp. 11879–11888 (1999).

*Primary Examiner*—Bruck Kifle
(74) *Attorney, Agent, or Firm*—P. C. Richardson; P. H. Ginsburg; A. D. Joran

(57) ABSTRACT

The present invention is directed to a compound of the formula (I):

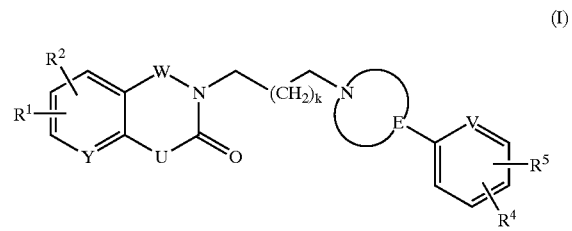

and pharmaceutically acceptable salts thereof, wherein $R^1$, $R^2$, Y, U, W, k, A, E, V, $R^4$ and $R^5$ are as defined herein, pharmaceutical compositions thereof, and methods of use thereof in the inhibition of serotonin reuptake, the inhibition of the binding of 5-HT$_{2A}$ serotonin receptors and the treatment of diseases, conditions or disorders of the central nervous system. Further, the present invention is also directed to methods for the preparation of compounds of formula (I) and intermediates useful therefor.

17 Claims, No Drawings

AZABICYCLOALKANE DERIVATIVES AND THERAPEUTIC USES THEREOF

This application claims the benefit of U.S. provisional application Ser. No. 60/222,707, filed Aug. 3, 2000.

The present invention is directed to 2-[(azabicycloalkyl)alkylenyl]isoquinolin-3-one derivatives and pharmaceutically acceptable salts thereof, to pharmaceutical compositions thereof, and to the use thereof to block selectively serotonin reuptake and 5-HT$_{2A}$ receptor binding in the central nervous system of a mammal. The present invention is also directed to the use of the 2-[(azabicycloalkyl)alkylenyl]isoquinolin-3-one derivatives of the invention in a method for the treatment of various diseases, disorders and conditions of the central nervous system. Further, the present invention is directed to processes for the preparation of said 2-[(azabicycloalkyl)alkylenyl]isoquinolin-3-one derivatives and intermediates useful therein.

Serotonin (5-hydroxytryptamine, "5-HT") is a monoamine neurotransmitter active in the central nervous systems of mammals, including humans. The cell bodies of serotoninergic cells are located in the brain stem, and the axons project therefrom into a variety of other areas, e.g., the amygdala, hippocampus, hypothalamus, nucleus accumbens and the striatum. Serotonin-producing cells store the neurotransmitter in intracellular vesicles, where it is either converted with monoamine oxidase ("MAO" EC 1.4.3.4) into 5-hydroxyindoleacetic acid ("5-HIAA") or released into synapses. In the synapses, serotonin is either resorbed into the presynaptic neurons and stored within intracellular vesicles of the presynaptic neurons or remains available for interaction with serotonin receptors, e.g., the 5-HT$_{2A}$ receptor, in post-synaptic membranes.

Altered functioning of this serotonin-based neurotransmission system has been implicated (see, e.g., Lancet, 2: 717–719 (1989)) in a variety of central nervous system related disorders, both psychiatric and non-psychiatric. These disorders include, without limitation, schizophrenia, psychosis, depression, aggression, sleep disorders, anxiety disorders, migraines, compulsive disorders, bipolar disorders, vision disorders, emesis, feeding disorders, learning disorders, sexual behavior disorders, phobias and substance abuse disorders. Compounds that either block serotonin reuptake into presynaptic neurons or that antagonize its interaction with post-synaptic membrane receptors have a wide variety of potential applications in the treatment of mammals, including humans, afflicted with central nervous system related disorders. The compounds act to restore some semblance of normal neurotransmitter functioning. Moreover, compounds which accomplish these objectives selectively can be used with a lower risk of attendant and unwanted side effects, e.g., sexual dysfunction, etc.

Shimazaki et al. (U.S. Pat. No. 5,296,487) describe quinazoline derivatives having activity as serotonergic, as well as alpha-adrenergic and dopaminergic, agents. Wade et al. (U.S. Pat. No. 4,007,191) describe tetrahydropyridylalkyl 2,3-dihydro-3-hydroxy-1H-benz(de)isoquinolin-1-ones having antidepressant activity. Hong et al. (U.S. Pat. No. 3,726,979) describe serotonin-antagonist quinazoline derivatives. Vidrio et al. (U.S. Pat. No. 3,919,425) indicate that certain 3-substituted 2,4-dioxoquinazolines have vasodilating activity. Shin et al. (U.S. Pat. No. 3,274,194) describe quinazolinedione derivatives that have anti-inflammatory and sedating activity. Moreover, Villalobos-Molina et al. (Eur. J. Pharmacol., 277(2/3): 181–5 (1995) and Drug Dev. Res., 23(3): 281–7 (1991)) describe 2,4-(1H, 3H)-quinazolinedione-3-[3-(4-phenyl-1-piperazinyl)propyl] (pelanserine) as having blood pressure lowering, 5-HT$_{2A}$ serotonin receptor binding activity. However, none of these documents describe or suggest either the 2-[(azabicycloalkyl)alkylenyl]isoquinolin-3-one compounds of the present invention, provided herein, or the therapeutic uses of the present invention.

SUMMARY OF THE INVENTION

The present invention provides a compound of formula (I):

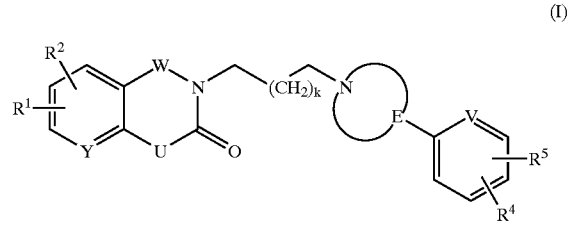

(I)

and pharmaceutically acceptable salts thereof, wherein the group

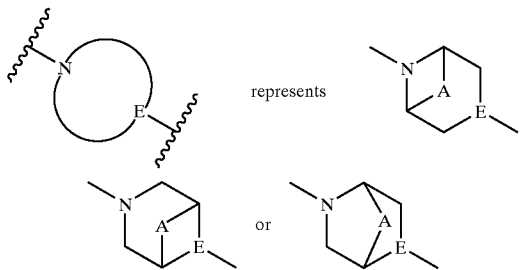

represents wherein

A is $(CH_2)_n$, where n is 1 or 2;

E is selected from the group consisting of N, CH, C—OH, C—CN, C—O—$(C_1$–$C_6)$alkyl, and C—$(C_1$–$C_6)$alkyl;

U is $CH_2$, NH, —$(CHR^3)_m$— or $NR^3$, where $R^3$ is selected from the group consisting of H, $(C_1$–$C_6)$alkyl and C(=O)—$(C_1$–$C_6)$alkyl;

m is 0 or 1;

k is 1 or 2;

$R^1$ and $R^2$ are selected independently from H, $(C_1$–$C_6)$ alkyl, halo, CN, nitro, $CF_3$, —NHC(O)$R^6$ and —$OR^7$, where $R^6$ and $R^7$ are selected independently from H, $(C_1$–$C_6)$alkyl, a 5- to 7-membered aryl ring, and a 5- to 7-membered heteroaryl ring; or $R^1$ and $R^2$, if on adjacent carbon atoms, together with the atoms to which they are attached, if adjacent, form a carbocyclic or heterocyclic five- or six-membered ring;

$R^4$ and $R^5$ are selected from H, $(C_1$–$C_6)$alkyl, halo, —$CF_3$, nitro, —CN, —NHC(=O)$R^6$, —$OR^7$, a 5- to 7-membered aryl ring, and a 5- to 7-membered heteroaryl ring; where $R^6$ and $R^7$ are as defined above;

V is CH, $CR^8$, or N, where $R^8$ is H, $(C_1$–$C_6)$alkyl, halo, —$CF_3$, nitro, —CN, —NHC(=O)$R^6$, —$OR^7$, a 5- to 7-membered aryl ring, or a 5- to 7-membered heteroaryl ring; wherein $R^6$ and $R^7$ are as defined above;

W is $CH_2$, C(O), or $S(O)_2$; and

Y is CH, $CR^1$, $CR^2$, or N, where $R^1$ and $R^2$ are as defined above.

Preferred compounds of formula (I) are those wherein

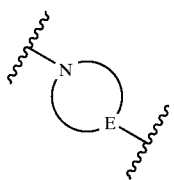 is 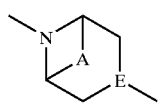 ;

A is $(CH_2)_n$ where n is equal to 1 or 2;
W is $C(=O)$;
Y is CH;
V is CH or N;
E is CH or N
U is NH; and
k, m, $R^1$, $R^2$, $R^3$, $R^4$, $R^5$, $R^6$, $R^7$ and $R^8$ are all as defined above.

Other preferred compounds are those wherein

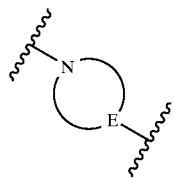 is 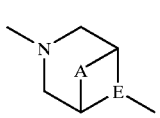 ;

A is $(CH_2)_n$ where n is equal to 1 or 2;
W is $C(=O)$;
Y is CH;
V is CH or N;
E is CH or N
U is NH; and
k, m, $R^1$, $R^2$, $R^3$, $R^4$, $R^5$, $R^6$, $R^7$ and $R^8$ are all as defined above.

Further preferred compounds are those wherein

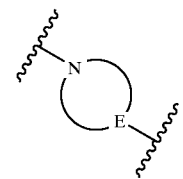 is 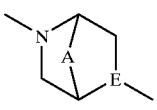 ;

A is $(CH_2)_n$ where n is equal to 1 or 2;
W is $C(=O)$;
Y is CH;
V is CH or N;
E is CH or N
U is NH; and
k, m, $R^1$, $R^2$, $R^3$, $R^4$, $R^6$, $R^7$ and $R^8$ are all as defined above.

More preferred compounds of formula (I) are those wherein

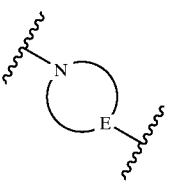 is 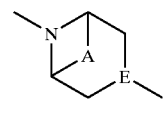 ;

A is $(CH_2)_n$ where n is equal to 2;
W is $C(=O)$;
Y is CH;
V is CH or N;
E is N
U is NH;
k is 1 or 2; and
$R^1$, $R^2$, $R^4$, and $R^5$ are independently chosen from the group consisting of hydrogen, halo, —$CF_3$, nitro, ($C_1$–$C_6$)alkyl, hydroxy and methoxy.

The most preferred embodiments of this invention, are compounds of formula (I) where

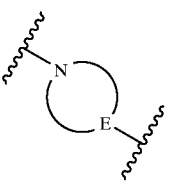 is 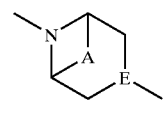 ;

A is $(CH_2)_n$ where n is 2;
k is 1;
E is N;
W is $C(=O)$;
Y is CH;
V is CH;
U is NH; and
$R^1$, $R^2$, $R^4$, and $R^5$ are independently chosen from the group consisting of hydrogen, hydroxy, methoxy, F, Cl, —$CF_3$, CN, nitro, ($C_1$–$C_6$)alkyl, a 5- to 7-membered aryl ring, and a 5- to 7-membered heteroaryl ring.

Specific embodiments of the invention are:
8-chloro-3-{3-[3-(4-chlorophenyl)-3,8-diazabicyclo[3.2.1] oct-8-yl]-propyl}-1H-quinazoline-2,4-dione;
8-chloro-3-[3-(8-p-tolyl-3,8-diazabicyclo[3.2.1]oct-3-yl)-propyl]-1H-quinazoline-2,4-dione;
8-chloro-3-{3-[8-(4-chloro-phenyl)-3,8-diazabicyclo[3.2.1] oct-3-yl]-propyl}-1H-quinazoline-2,4-dione;
3-{3-[3-(4-chloro-phenyl)-3,8-diazabicyclo[3.2.1]oct-8-yl]-propyl}-6-methyl-1H-quinazoline-2,4-dione;
3-{3-[3-(4-chloro-phenyl)-3,8-diazabicyclo[3.2.1]oct-8-yl]-propyl}-1H-quinazoline-2,4-dione;
3-[3-(3-p-tolyl-3,8-diazabicyclo[3.2.1]oct-8-yl)-propyl]-1H-quinazoline-2,4-dione;
3-{3-[3-(4-chloro-phenyl)-8-azabicyclo[3.2.1]oct-8-yl]-propyl}-1H-quinazoline-2,4-dione;
3-[3-(3-phenyl-8-azabicyclo[3.2.1]oct-8-yl)-propyl]-1H-quinazoline-2,4-dione;
3-[3-(3-p-tolyl-8-azabicyclo[3.2.1]oct-8-yl)-propyl]-1H-quinazoline-2,4-dione;
8-chloro-3-[3-(3-p-tolyl-3,8-diazabicyclo[3.2.1]oct-3-yl)-propyl]-1H-quinazoline-2,4-dione;
8-chloro-3-{3-[3-(2,4-dimethyl-phenyl)-3,8-diazabicyclo [3.2.1]oct-8-yl]-propyl}-1H-quinazoline-2,4-dione;

8-chloro-3-{3-[3-(3,4-dichloro-phenyl)-3,8-diazabicyclo [3.2.1]oct-8-yl]-propyl}-1H-quinazoline-2,4-dione;
3-{3-[3-(3,4-dichloro-phenyl)-3,8-diazabicyclo[3.2.1]oct-8-yl]-propyl}-1H-quinazoline-2,4-dione;
8-chloro-3-{3-[3-(4-fluoro-phenyl)-3,8-diazabicyclo[3.2.1] oct-8-yl]-propyl}-1H-quinazoline-2,4-dione;
3-{3-[3-(4-fluoro-phenyl)-3,8-diazabicyclo[3.2.1]oct-8-yl]-propyl}-1H-quinazoline-2,4-dione;
8-chloro-3-{3-[3-(4-trifluoromethyl-phenyl)-3,8-diazabicyclo[3.2.1]oct-8-yl]-propyl}-1H-quinazoline-2,4-dione;
3-{3-[3-(4-trifluoromethyl-phenyl)-3,8-diazabicyclo[3.2.1] oct-8-yl]-propyl}-1H-quinazoline-2,4-dione;
6,7-difluoro-3-[3-(3-p-tolyl-3,8-diazabicyclo[3.2.1]oct-8-yl)-propyl]-1H-quinazoline-2,4-dione;
6-fluoro-3-[3-(3-p-tolyl-3,8-diazabicyclo[3.2.1]oct-8-yl)-propyl]-1H-quinazoline-2,4-dione;
8-chloro-3-{4-[3-(4-chloro-phenyl)-3,8-diazabicyclo[3.2.1] oct-8-yl]-butyl}-1H-quinazoline-2,4-dione;
3-{4-[3-(4-chloro-phenyl)-3,8-diazabicyclo[3.2.1]oct-8-yl]-butyl}-6-methyl-1H-quinazoline-2,4-dione;
3-{4-[3-(4-chloro-phenyl)-3,8-diazabicyclo[3.2.1]oct-8-yl]-butyl}-1H-quinazoline-2,4-dione;
8-chloro-3-{3-[8-(4-chloro-phenyl)-3,8-diazabicyclo[3.2.1] oct-3-yl]-propyl}-1H-quinazoline-2,4-dione;
8-chloro-3-{3-[5-(4-chloro-phenyl)-2,5-diazabicyclo[2.2.1] hept-2-yl]-propyl}-1H-quinazoline-2,4-dione;
8-chloro-3-{3-[5-(3-fluoro-phenyl)-2,5-diazabicyclo[2.2.1] hept-2-yl]-propyl}-1H-quinazoline-2,4-dione;
8-chloro-3-{3-[5-(4-fluoro-phenyl)-2,5-diazabicyclo[2.2.2] oct-2-yl]-propyl}-1H-quinazoline-2,4-dione;
8-chloro-3-{3-[5-(2,4-dimethyl-phenyl)-2,5-diazabicyclo [2.2.2]oct-2-yl]-propyl}-1H-quinazoline-2,4-dione;
8-chloro-3-{3-[5-(3,4-dichlorophenyl)-2,5-diazabicyclo [2.2.2]oct-2-yl]-propyl}-1H-quinazoline-2,4-dione;
3-{3-[5-(4-fluorophenyl)-2,5-diazabicyclo[2.2.2]oct-2-yl]-propyl}-1H-quinazoline-2,4-dione;
and pharmaceutically acceptable salts thereof.

The present invention also provides a method for treating a disease, disorder or condition in a mammal that can be treated by inhibiting serotonin reuptake or serotonin 5-HT$_{2A}$ receptor binding in the central nervous system of a mammal, comprising the administration to the mammal a serotonin 5-HT$_{2A}$ receptor binding-inhibiting effective amount or a serotonin reuptake-inhibiting effective amount of a compound of formula (I) or a pharmaceutically acceptable salt thereof.

The present invention further provides a method for treating a disease, disorder or condition in a mammal that can be treated by inhibiting serotonin reuptake or serotonin 5-HT$_{2A}$ receptor binding in the central nervous system of a mammal, comprising the administration to the mammal an amount of a compound of formula (I) or a pharmaceutically acceptable salt thereof, effective to treat the disease, disorder or condition.

The present invention further provides a method of treating in a mammal a disease, disorder or condition selected from the group consisting of aggression disorders; anxiety disorders (e.g., panic attack, agoraphobia, panic disorder with or without agoraphobia, agoraphobia without history of panic disorder, specific phobia, social phobia, obsessive-compulsive disorder, post-traumatic stress disorder and acute stress disorder); cognitive disorders selected from the group consisting of amnestic disorders (e.g., amnestic disorders due to a general medical condition, substance-induced persisting amnestic disorder and amnestic disorders not otherwise specified), deliriums (e.g., deliriums due to a general medical condition, substance-induced delirium and delirium not otherwise specified), dementias (e.g., dementia of the Alzheimer's type, vascular dementia, dementia due to a general medical condition (e.g., AIDS-, Parkinson's-, head trauma-, and Huntington's-induced dementias), substance-induced persisting dementia, dementia due to multiple etiologies, and dementia not otherwise specified) and cognitive disorders not otherwise specified; depression disorders; emesis; epilepsy; food-related behavioral disorders, including anorexia nervosa and bulimia; headache disorders selected from the group consisting of migraine, cluster and vascular headaches; learning disorders, including attention deficit disorder and attention deficit/hyperactivity disorder; obesity; ocular disorders; platelet aggregation disorders; psychotic conditions selected from the group consisting of schizophrenia (e.g., paranoid-type, disorganized-type, catatonic-type, undifferentiated-type and residual-type), schizophreniform disorder, schizoaffective disorder, delusional disorder, brief psychotic disorder, shared psychotic disorder, psychotic disorders due to a general medical condition and psychotic disorders not otherwise specified; sleep disorders selected from the group consisting of primary sleep disorders (e.g., parasomnias and dyssomnias), sleep disorders related to another mental disorder (including, without limitation, mood and anxiety disorders), sleep disorders due to a general medical condition and sleep disorders not otherwise specified; sexual behavior disorders; substance-abuse disorders selected from the group consisting of alcohol-related disorders, including alcohol-use disorders (e.g., dependence and abuse disorders) and alcohol-induced disorders (e.g., intoxication, withdrawal, intoxication delirium, withdrawal delirium, persisting dementia, persisting amnestic, mood, anxiety, sexual dysfunction, sleep and not otherwise specified disorders), amphetamine-related disorders, including amphetamine-use disorders (e.g., dependence and abuse disorders) and amphetamine-induced disorders (e.g., intoxication, withdrawal, intoxication delirium, psychotic, mood, anxiety, sexual dysfunction, sleep and not otherwise-specified disorders), caffeine-related disorders, such as intoxication, induced-anxiety disorder, induced-sleep disorder and disorders not otherwise specified; cannabis-related disorders, including cannabis-use disorders (e.g., abuse and dependence disorders) and cannabis-induced disorders (e.g., intoxication, intoxication delirium, psychotic, anxiety and not otherwise specified disorders), cocaine-related disorders, including cocaine-use disorders (e.g., dependence and abuse disorders) and cocaine-induced disorders (e.g., intoxication, withdrawal, intoxication delirium, psychotic, mood, anxiety, sexual dysfunction, sleep and not otherwise specified disorders), hallucinogen-related disorders, including hallucinogen-use disorders (e.g., dependence and abuse disorders) and hallucinogen-induced disorders (e.g., intoxication, persisting perception, intoxication delirium, psychotic, mood, anxiety and not otherwise specified disorders), inhalant-related disorders, including inhalant-use disorders (e.g., dependence and abuse disorders) and inhalant-induced disorders (e.g., intoxication, intoxication delirium, persisting dementia, psychotic, mood, anxiety and not otherwise specified disorders), nicotine-related disorders, such as dependence, withdrawal and not otherwise specified disorders, opioid related disorders, including opioid-use disorders (e.g., dependence and abuse disorders) and opioid-induced disorders (e.g., intoxication, withdrawal, intoxication delirium, psychotic, mood, sexual dysfunction, sleep and not otherwise-specified disorders), phencyclidine-related disorders, including phencyclidine-use disorders (e.g., dependence and abuse disorders) and phencyclidine-induced disorders (e.g., intoxication, intoxication delirium, psychotic, mood, anxiety and not otherwise-specified disorders), sedative-, hypnotic- or anxiolytic-related disorders, including sedative-use disorders (e.g., dependence and abuse disorders) and sedative-induced disorders (e.g., intoxication, withdrawal, intoxication delirium, withdrawal delirium, persisting dementia, persisting amnestic, psychotic, mood, anxiety, sexual dysfunction, sleep and not otherwise specified disorders), polysubstance-related disorder, other substance dependence and abuse disorders, and other substance-induced disorders (e.g., intoxication, withdrawal, delirium, persisting dementia, persisting amnestic, psychotic, mood, anxiety, sexual dysfunction, sleep and not otherwise specified disorders); and vision disorders, including glaucoma; comprising administering to the mammal a serotonin 5-$HT_{2A}$ receptor binding-inhibiting effective amount or a serotonin reuptake-inhibiting effective amount of a compound of formula (I) or a pharmaceutically acceptable salt thereof.

The present invention further provides a method of treating in a mammal a disease, disorder or condition, selected from the list set forth in the previous paragraph, comprising administering to the mammal an amount of a compound of formula (I) or a pharmaceutically acceptable salt thereof effective to treat the disease, disorder or condition.

Further provided herein is a pharmaceutical composition comprising a compound of formula (I) and a pharmaceutically acceptable carrier. Still further provided is a pharmaceutical composition for selectively inhibiting serotonin reuptake or serotonin receptor binding in the central nervous system of a mammal, said composition comprising a pharmaceutically acceptable carrier and a serotonin reuptake-inhibiting effective amount or a serotonin receptor binding-inhibiting effective amount of a compound of formula (I).

The present invention also relates to a process for preparing compounds of formula (I). More specifically, the invention relates to a process for preparing a compound of formula (I) comprising the step of reacting a compound of formula (AII)

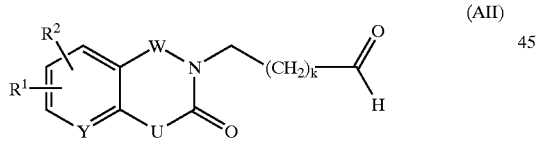
(AII)

wherein
k is 1 or 2;
U is $CH_2$, NH, —$(CHR^3)_m$— or $NR^3$, where $R^3$ is selected from the group consisting of H, $(C_1-C_6)$ alkyl, and C(=O)—$(C_1-C_6)$alkyl;
m is 0 or 1;
W is $CH_2$, C(O), or $S(O)_2$;
Y is CH, $CR^1$, $CR^2$, or N, where $R^1$ and $R^2$ are as defined above
$R^1$ and $R^2$ are selected independently from H, $(C_1-C_6)$ alkyl, halo, CN, nitro, $CF_3$, —NHC(O)$R^6$ and —$OR^7$, where $R^6$ and $R^7$ are selected independently from H, $(C_1-C_6)$alkyl, a 5- to 7-membered aryl ring, and a 5- to 7-membered heteroaryl ring, or
$R^1$ and $R^2$, together with the atoms to which they are attached, if adjacent to one another, form a carbocyclic or heterocyclic five- or six-membered ring;

with a compound of formula (BI)

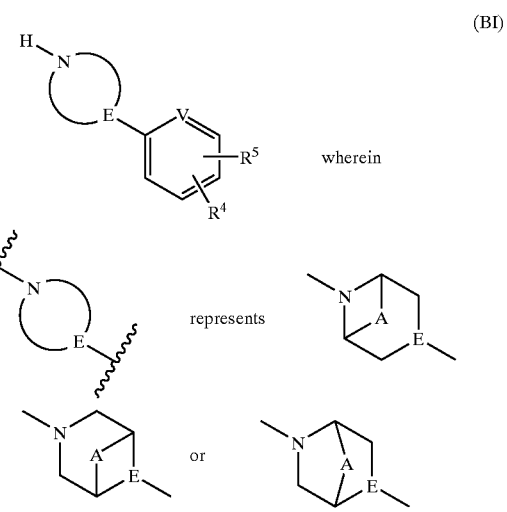
(BI)

wherein, for each,
A is $(CH_2)_n$ where n is 1 or 2;
E is selected from the group consisting of N, CH, C—OH, C—CN, C—O—$(C_1-C_6)$alkyl, and C—$(C_1-C_6)$alkyl;
U is $CH_2$, NH, —$(CHR^3)_m$— or $NR^3$, where $R^3$ is selected from the group consisting of H, $(C_1-C_6)$ alkyl and C(=O)—$(C_1-C_6)$alkyl;
m is 0 or 1;
k is 1 or 2;
$R^1$ and $R^2$ are selected independently from H, $(C_1-C_6)$ alkyl, halo, CN, nitro, $CF_3$, —NHC(O)$R^6$ and —$OR^7$, where $R^6$ and $R^7$ are selected independently from H, $(C_1-C_6)$alkyl, a 5- to 7-membered aryl ring, and a 5- to 7-membered heteroaryl ring; or $R^1$ and $R^2$, if on adjacent carbon atoms, together with the atoms to which they are attached, if adjacent, form a carbocyclic or heterocyclic five- or six-membered ring;
$R^4$ and $R^5$ are selected from H, $(C_1-C_6)$alkyl, halo, —$CF_3$, nitro, —CN, —NHC(=O)$R^6$, —$OR^7$, a 5- to 7-membered aryl ring, and a 5- to 7-membered heteroaryl ring; where $R^6$ and $R^7$ are as defined above;
V is CH, $CR^8$, or N, where $R^8$ is H, $(C_1-C_6)$alkyl, halo, —$CF_3$, nitro, —CN, —NHC(=O)$R^6$, —$OR^7$, a 5- to 7-membered aryl ring, or a 5- to 7-membered heteroaryl ring; wherein $R^6$ and $R^7$ are as defined above;
W is $CH_2$, C(O), or $S(O)_2$; and
Y is CH, $CR^1$, $CR^2$, or N, where $R^1$ and $R^2$ are as defined above.

The present invention also relates to a process for the preparation of a compound of formula (I), wherein U is NH; and W is C(O) or $SO_2$, comprising the steps of
(a) allowing a compound of formula (AIII)

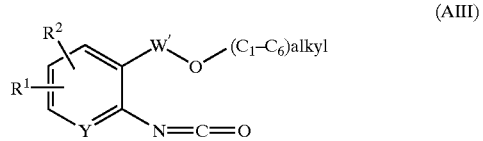
(AIII)

wherein W' is C(O), or $S(O)_2$; Y is CH, $CR^1$, $CR^2$, or N, and $R^1$ and $R^2$ are selected independently from H, ($C_1$–$C_6$)alkyl, halo, CN, nitro, $CF_3$, —NHC(O)$R^6$ and —O$R^7$, where $R^6$ and $R^7$ are selected independently from H, ($C_1$–$C_6$)alkyl, a 5- to 7-membered aryl ring and a 5- to 7-membered heteroaryl ring, or $R^1$ and $R^2$, together with the atoms to which they are attached, if adjacent, form a carbocyclic or heterocyclic five- or six-membered ring;

to react with a compound of formula (BII)

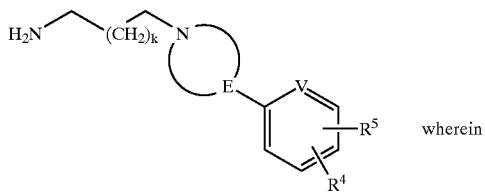

(BII)

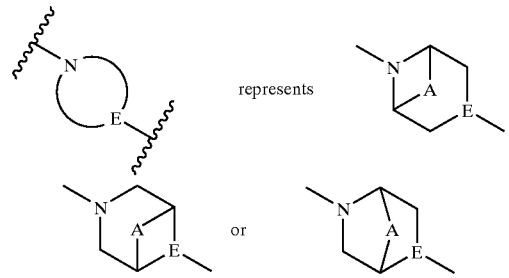

represents wherein
A is $(CH_2)_n$ where n is 1 or 2;
k is 1 or 2;
E is selected from the group consisting of N, CH, C—OH, C—CN, C—O—($C_1$–$C_6$)alkyl, and C—($C_1$–$C_6$)alkyl;
V is CH, $CR^3$, or N, where $R^3$ is as defined above; and $R^4$ and $R^5$ are selected from H, ($C_1$–$C_6$)alkyl, halo, —$CF_3$, —CN, —NHC(=O)$R^6$, —O$R^7$, a 5- to 7-membered aryl ring, and a 5- to 7-membered heteroaryl ring, where $R^6$ and $R^7$ are as defined above;

to form a compound of formula (CI)

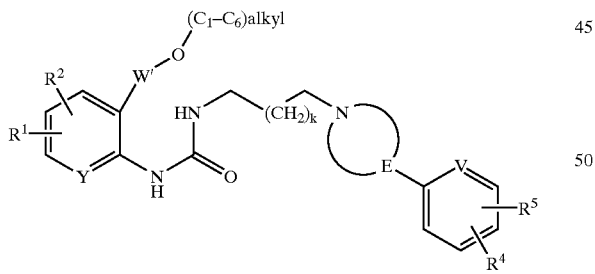

(CI)

k, $R^1$, $R^2$, Y, W', A, E, V, $R^4$, and R5 are as defined above; and (b) allowing a compound of formula (CI) to undergo a ring closure reaction (i.e., to form the quinazoline ring) to form a compound of formula (I).

The present invention also relates to a process for the preparation of compounds of formula (I), wherein U is NH; W is C(O); comprising the steps of (a) allowing a compound of formula (DIII)

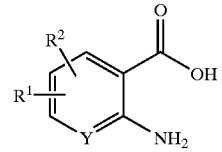

(DIII)

wherein Y, $R^1$ and $R^2$ are as defined above;

to react with a halo($C_3$–$C_4$)alkylisocyanate of the formula X—$(CH_2)_{k+2}$NCO, wherein k is 1 or 2, and X is halo, to form a compound of formula (GI)

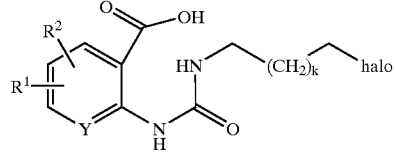

(GI)

wherein Y, $R^1$, $R^2$ and k are as defined above;

(b) allowing the compound of formula (GI) to undergo a double ring closure reaction (ie., forming simultaneously a diamide containing- and an oxo-ring) to form a tricyclic compound of formula (FI)

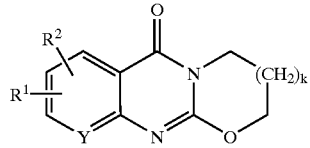

(FI)

wherein $R^1$, $R^2$ and Y are as defined above;

and (c) further permitting (FI) to react with a compound of formula (BI)

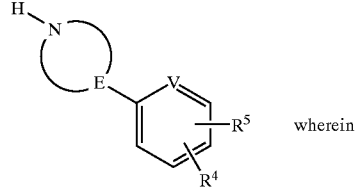

(BI)

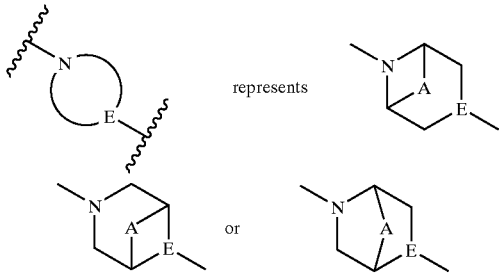

represents and E, V and $R^4$ and $R^5$ are as defined above, or a salt thereof.

A preferred process of the invention is any one of the three processes above wherein

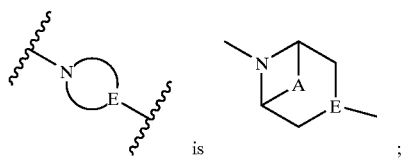
is
;

A is $(CH_2)_n$ where n is equal to 1 or 2;
W is $C(=O)$;
Y is CH;
V is CH or N;
E is CH or N
U is NH; and
k, m, $R^1$, $R^2$, $R^3$, $R^4$, $R^5$, $R^6$, $R^7$ and $R^8$ are all as defined above.

Another preferred process is any one of the processes above wherein

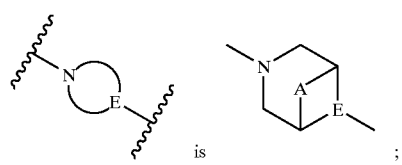
is
;

A is $(CH_2)_n$ where n is equal to 1 or 2;
W is $C(=O)$;
Y is CH;
V is CH or N;
E is CH or N
U is NH; and
k, m, $R^1$, $R^2$, $R^3$, $R^4$, $R^5$, $R^6$, $R^7$ and $R^8$ are all as defined above.

A further preferred process is any one of the processes above wherein

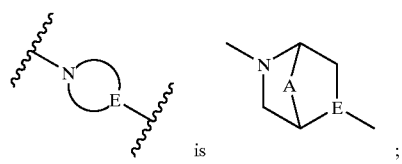
is
;

A is $(CH_2)_n$ where n is equal to 1 or 2;
W is $C(=O)$;
Y is CH;
V is CH or N;
E is CH or N
U is NH; and
k, m $R^1$, $R^2$, $R^3$, $R^4$, $R^5$, $R^6$, $R^7$ and $R^8$ are all as defined above.

A more preferred process is any one of the processes above wherein

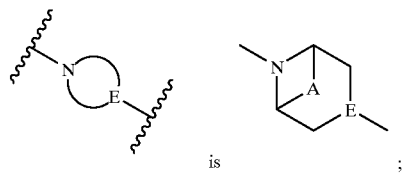
is
;

A is $(CH_2)_n$ where n is equal to 2;
W is $C(=O)$;
Y is CH;
V is CH or N;
E is N
U is NH;
k is 1 or 2; and
$R^1$, $R^2$, $R^4$, and $R^5$ are independently chosen from the group consisting of hydrogen, halo, —$CF_3$, nitro, $(C_1-C_6)$alkyl, hydroxy and methoxy.

The most preferred process is any one of the three processes above wherein

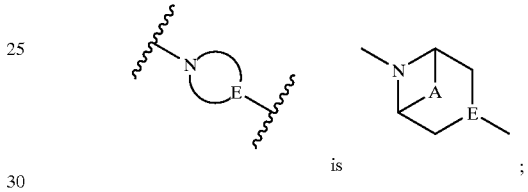
is
;

A is $(CH_2)_n$ where n is 2;
k is 1;
E is N;
W is $C(=O)$;
Y is CH;
V is CH;
U is NH; and
$R^1$, $R^2$, $R^4$, and $R^5$ are independently chosen from the group consisting of hydrogen, hydroxy, methoxy, F, Cl, —$CF_3$, CN, nitro, $(C_1-C_6)$alkyl, a 5- to 7-membered aryl ring, and a 5- to 7-membered heteroaryl ring.

In the foregoing description of the invention and throughout this application, the following terms have the stated meanings, unless otherwise indicated: "alkyl" means saturated monovalent hydrocarbon radicals having straight, branched or cyclic moieties, or combinations thereof; "halo" and "halogen" means chloro, fluoro, bromo or iodo; "treating" refers to, and includes, reversing, alleviating, inhibiting the progress of, or preventing a disease, disorder or condition, or one or more symptoms thereof; and, "treatment" and "therapeutically" refer to the act of treating, as defined above.

The term "carbocyclic 5- to 7-member ring," unless otherwise indicated, means any member of cyclopentyl, cyclohexyl, or cycloheptyl monocyclic ring system, with or without at least one point of unsaturation. The term "heterocyclic 5- to 7-membered ring," unless otherwise indicated, means a cyclopentyl, cyclohexyl, or cycloheptyl monocyclic ring system wherein one to three of the carbon atoms is replaced by a nitrogen, oxygen or sulfur atom, with or without one point of unsaturation.

The term "5- to 7-membered aryl ring," unless otherwise indicated, means an unsaturated 5- to 7-membered carbocyclic monocyclic ring system, including but not limited to phenyl. The term "5- to 7-membered heteroaryl ring," unless otherwise indicated, means an unsaturated 5- to 7-membered monocyclic ring system wherein one to three of the ring members is a nitrogen, oxygen or sulfur atom and the remaining ring members are carbon atoms, including but not limited to thienyl, furanyl, pyrrolyl, thiazolyl, oxazolyl, isothiazolyl, isoxazolyl, imidazolyl, pyrimidinyl, and pyridinyl.

The various "diseases, disorders and conditions" to which the compositions and methods of this invention are directed include, without limitation: aggression disorders; anxiety disorders selected from the group consisting of panic attack, agoraphobia, panic disorder with or without agoraphobia, agoraphobia without history of panic disorder, specific phobia, social phobia, obsessive-compulsive disorder, post-traumatic stress disorder and acute stress disorder; cognitive disorders selected from the group consisting of amnestic disorders (e.g., amnestic disorders due to a general medical condition, substance-induced persisting amnestic disorder and amnestic disorders not otherwise specified), deliriums (e.g., deliriums due to a general medical condition, substance-induced delirium and delirium not otherwise specified), dementias (e.g., dementia of the Alzheimer's type, vascular dementia, dementia due to a general medical condition (e.g., AIDS-, Parkinson's-, head trauma-, and Huntington's-induced dementias), substance-induced persisting dementia, dementia due to multiple etiologies, and dementia not otherwise specified) and cognitive disorders not otherwise specified; depression disorders; emesis; epilepsy; food-related behavioral disorders, including anorexia nervosa and bulimia; headache disorders selected from the group consisting of migraine, cluster and vascular headaches; learning disorders, including attention deficit disorder and attention deficit/hyperactivity disorder; obesity; ocular disorders; platelet aggregation disorders; psychotic conditions selected from the group consisting of schizophrenia (e.g., paranoid-type, disorganized-type, catatonic-type, undifferentiated-type and residual-type), schizophreniform disorder, schizoaffective disorder, delusional disorder, brief psychotic disorder, shared psychotic disorder, psychotic disorders due to a general medical condition and psychotic disorders not otherwise specified; sleep disorders selected from the group consisting of primary sleep disorders (e.g., parasomnias and dyssomnias), sleep disorders related to another mental disorder (including, without limitation, mood and anxiety disorders), sleep disorders due to a general medical condition and sleep disorders not otherwise specified; sexual behavior disorders; substance-abuse disorders selected from the group consisting of alcohol-related disorders, including alcohol-use disorders (e.g., dependence and abuse disorders) and alcohol-induced disorders (e.g., intoxication, withdrawal, intoxication delirium, withdrawal delirium, persisting dementia, persisting amnestic, mood, anxiety, sexual dysfunction, sleep and not otherwise specified disorders), amphetamine-related disorders, including amphetamine-use disorders (e.g., dependence and abuse disorders) and amphetamine-induced disorders (e.g., intoxication, withdrawal, intoxication delirium, psychotic, mood, anxiety, sexual dysfunction, sleep and not otherwise-specified disorders), caffeine-related disorders, such as intoxication, induced-anxiety disorder, induced-sleep disorder and disorders not otherwise specified; cannabis-related disorders, including cannabis-use disorders (e.g., abuse and dependence disorders) and cannabis-induced disorders (e.g., intoxication, intoxication delirium, psychotic, anxiety and not otherwise specified disorders), cocaine-related disorders, including cocaine-use disorders (e.g., dependence and abuse disorders) and cocaine-induced disorders (e.g., intoxication, withdrawal, intoxication delirium, psychotic, mood, anxiety, sexual dysfunction, sleep and not otherwise specified disorders), hallucinogen-related disorders, including hallucinogen-use disorders (e.g., dependence and abuse disorders) and hallucinogen-induced disorders (e.g., intoxication, persisting perception, intoxication delirium, psychotic, mood, anxiety and not otherwise specified disorders), inhalant-related disorders, including inhalant-use disorders (e.g., dependence and abuse disorders) and inhalant-induced disorders (e.g., intoxication, intoxication delirium, persisting dementia, psychotic, mood, anxiety and not otherwise specified disorders), nicotine-related disorders, such as dependence, withdrawal and not otherwise specified disorders, opioid related disorders, including opioid-use disorders (e.g., dependence and abuse disorders) and opioid-induced disorders (e.g., intoxication, withdrawal, intoxication delirium, psychotic, mood, sexual dysfunction, sleep and not otherwise-specified disorders), phencyclidine-related disorders, including phencyclidine-use disorders (e.g., dependence and abuse disorders) and phencyclidine-induced disorders (e.g., intoxication, intoxication delirium, psychotic, mood, anxiety and not otherwise-specified disorders), sedative-, hypnotic- or anxiolytic-related disorders, including sedative-use disorders (e.g., dependence and abuse disorders) and sedative-induced disorders (e.g., intoxication, withdrawal, intoxication delirium, withdrawal delirium, persisting dementia, persisting amnestic, psychotic, mood, anxiety, sexual dysfunction, sleep and not otherwise specified disorders), polysubstance-related disorder, other substance dependence and abuse disorders, and other substance-induced disorders (e.g., intoxication, withdrawal, delirium, persisting dementia, persisting amnestic, psychotic, mood, anxiety, sexual dysfunction, sleep and not otherwise specified disorders); vision disorders, including glaucoma; and, various additional diseases, disorders and conditions as well.

"Pharmaceutically acceptable salts" or "pharmaceutically acceptable acid addition salts" of compounds of this invention may be made from those acids which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

Compounds of formula (I) may contain chiral centers, and therefore may exist in different enantiomeric and diastereomeric forms; this invention is directed to all such optical and stereoisomers of compounds of formula (I), as well as mixtures thereof, and to all pharmaceutical compositions and methods of treatment that contain or employ them.

This invention is also directed to isotopically-labeled compounds identical to those recited in formula (I), or pharmaceutically acceptable salts thereof, but for the fact that one or more atoms are replaced therein by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

Compounds of the present invention, prodrugs thereof, and pharmaceutically acceptable salts of said compounds, or of said prodrugs, which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful, for example, in drug and/or substrate tissue distribution assays. Tritiated, i.e., $^3H$, and carbon-14, i.e., $^{14}C$, isotopes are particularly preferred for their ease of preparation and detectability. Furthermore, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

Isotopically labeled compounds of formula (I) of this invention and prodrugs thereof can generally be prepared by carrying out the procedures set forth below, by substituting a readily available isotopically labeled reagent for a non-isotopically labeled reagent.

DETAILED DESCRIPTION OF THE INVENTION

Compounds of formula (I) may be prepared as described below, wherein, unless otherwise indicated, A, E, U, V, W, X, Y, $R^1$, $R^2$, $R^3$, $R^4$, $R^5$, $R^6$, $R^7$, k, and n and the structural formula (I) in the discussion that follows are defined as above. Compounds of the formula (I) may be prepared by processes outline according to the schemes set forth below:

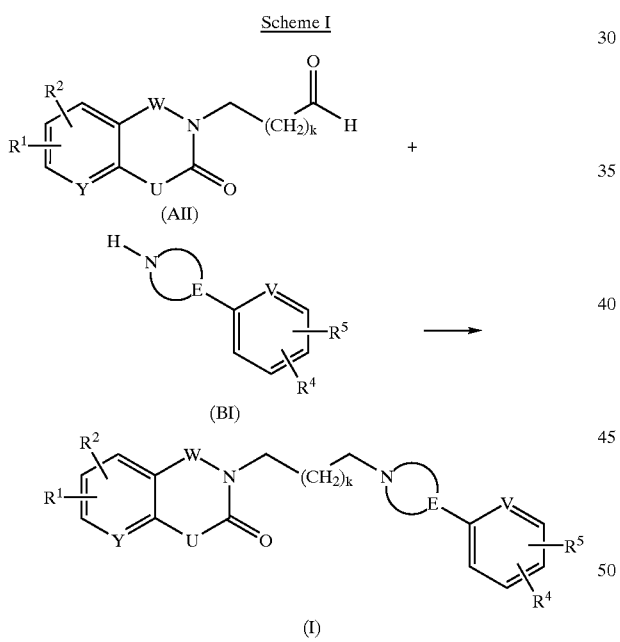

In Scheme I, compounds of formula (I) are prepared by reacting a compound of formula (AII), wherein W, Y, U, $R^1$, $R^2$ and k are as defined above, under reductive amination conditions with a compound of the general formula (BI), wherein V, A, E, $R^4$ and $R^5$ are as defined above. The reaction of Scheme Ia may be carried out in a solvent, such as, e.g., lower alcohols, cyclic and acyclic mono- and dialkylamides, acetonitrile, cyclic and acyclic alkyl ethers, or aromatic solvents (e.g., benzene, toluene, etc.), at a temperature in the range of 0° C. to 150° C.

A compound of the general formula (AII) wherein k is 3 utilized in the reaction of Scheme I may be readily prepared from a compound of the general formula (AI):

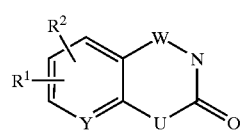

wherein U, W, Y, $R^1$, and $R^2$ are as defined above, by allowing it to react with an appropriate α,β-unsaturated aldehyde or ketone in a suitable solvent, e.g., cyclic or acyclic monoalkylamides or dialkylamides, $C_1$–$C_4$ alcohols, and mixtures thereof, at reaction temperatures in the range of 0° C. to 150° C., more preferably in the range from about 0° C. up to the boiling point of the solvent or solvent mixture used. The presence of acid acceptors, e.g., alkali carbonates, tertiary amines, etc., is often helpful in such reactions. The compound (AI) may be either obtained from commercial sources or prepared from known and readily available materials.

As shown in Schemes II, II-A, II-B and II-C below, compounds of formula (BI) may be readily prepared. In Scheme II, a compound of formula (EI), a subgenus of the compounds of formula (BI), wherein

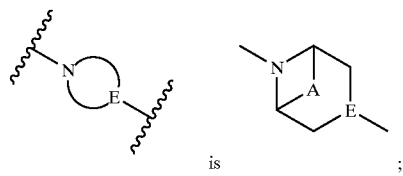

E is N, and V, $R^4$ and $R^5$ are as defined above, is prepared.

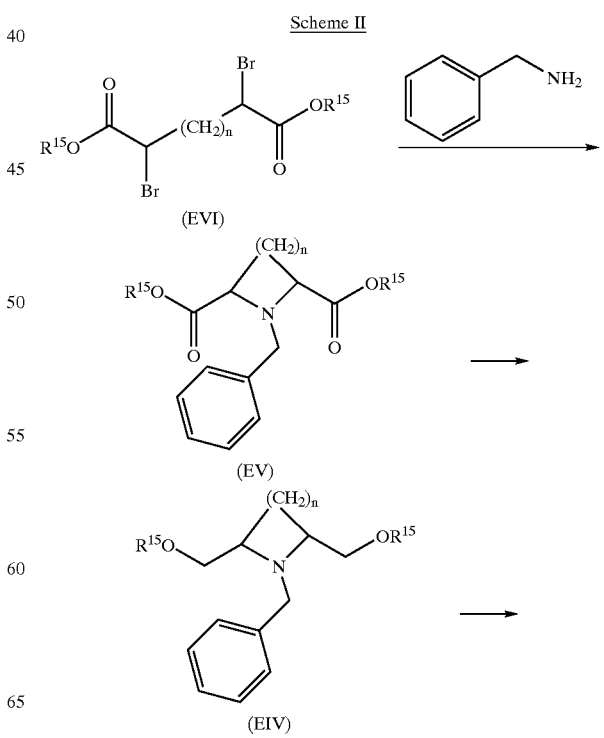

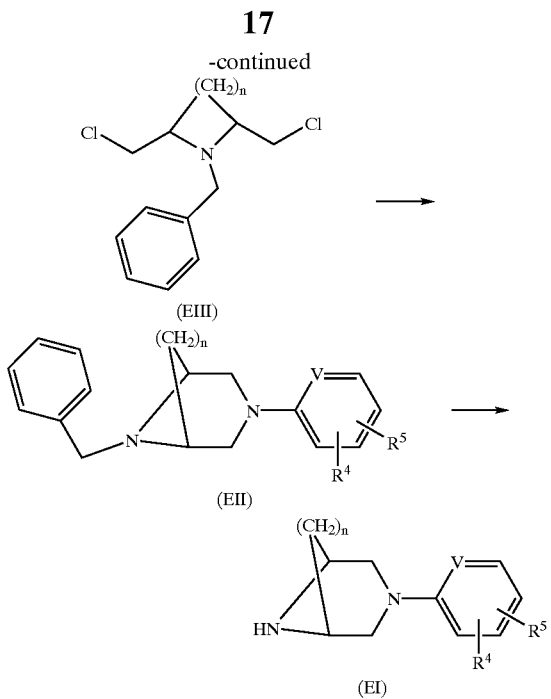

Referring to Scheme II, a compound of general formula EVI, wherein $R^{15}$ is H or $(C_1-C_6)$alkyl, and n is 1 or 2, is allowed to react with benzylamine in presence of a base, e.g., triethylamine, potassium carbonate, etc., to provide a compound of general formula EV at a temperature ranging from ambient temperature to the reflux temperature of a solvent or a mixture of solvents selected from the group consisting of dimethylformamide, acetonitrile, chloroform, dioxane, acetone, water, or lower alcohols (e.g., propanol ethanol, methanol, etc.). The compound of general formula EV formed in the first step is then transformed into the protected diol derivative of the formula EIV in the presence of a reducing agents such as, for example, an aluminum hydride or a borohydride, at a temperature ranging from ambient temperature to the reflux temperature of a solvent or a mixture of solvents selected from the group consisting of lower alkyl (e.g., $(C_1-C_6)$alkyl) alcohols, lower cyclic or acyclic alkyl ethers or dioxane. The compound of formula EIV is then in turn converted into the dichloride compound of formula EIII via treatment with a reagent, such as, e.g., $SO_2Cl_2$, $POCl_3$ or similar chlorinating reagents, in the absence of a solvent or in a halogenated solvent such as chloroform, carbon tetrachloride or methylene chloride at a temperature ranging from ambient temperature to the reflux temperature of any one of said halogenated solvents or mixtures thereof. The compound of formula EIII is converted to a compound of formula EII via the reaction of the compound of formula EIII with excess of an arylamine of the formula

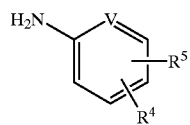

wherein V, $R^4$ and $R^5$ are as defined above, in presence or absence of a solvent, or in a solvent or mixture of solvents selected from dimethyl formamide, dioxane, N,N-dimethylacetamide and pyrrolidinone, at a temperature ranging from room temperature to the reflux temperature of any of those solvents or mixtures thereof. Finally, the compound of general formula EII is then transformed to a compound of general formula EI by removing the benzyl grouping using hydrogen gas in presence of a catalyst selected from the group consisting of palladium on carbon, platinum oxide or similar reagents in a solvents or mixture of solvents selected from the group consisting of lower cyclic or acyclic alkyl alcohols, lower cyclic or acyclic alkyl ethers, water, acetic acid, formic acid, hydrochloric acid or dimethyl formamide, at a temperature ranging from ambient temperature to the reflux temperatures of said solvent or mixture of solvents, at a hydrogen gas pressure ranging from 0 to 5 atmospheres. Compounds of general formula EI are converted into compounds of general formula (I) using procedures which are essentially identically as those described in Scheme I.

As shown in Scheme II-A, compounds of the general formula (BI), wherein

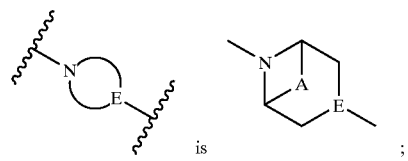

A and V are as defined above, and E is C—OH, C—O—$(C_1-C_6)$alkyl, C—CN or C—H, are prepared by reacting easily prepared or commercially available piperidine-4-one compounds of the general formula (EIB), wherein A is as defined above, and $R^9$ denotes a nitrogen-protecting group, with an aryl or heteroaryl group transferring reagent of the general formula (EIA), wherein M denotes a metal such as for example $Li^+$, $Mg^{2+}$, etc., and V, $R^4$ and $R^5$ are as define above, to provide intermediates of the general formula (DI).

Scheme II-A

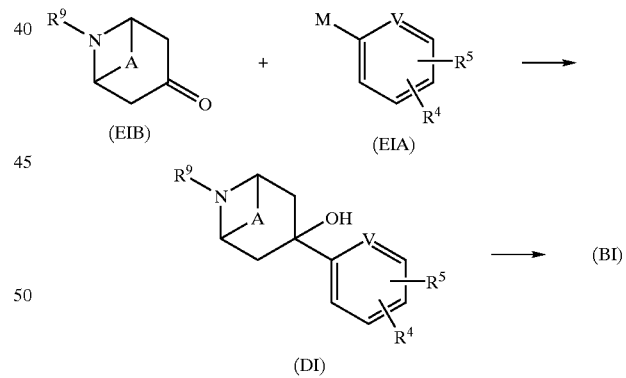

Compounds of the general formula (DI), may then be converted into a compounds of formula (BI), where

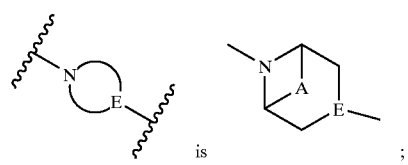

and E is C—OH, via removal of the nitrogen protecting group. Compounds of formula (BI), where

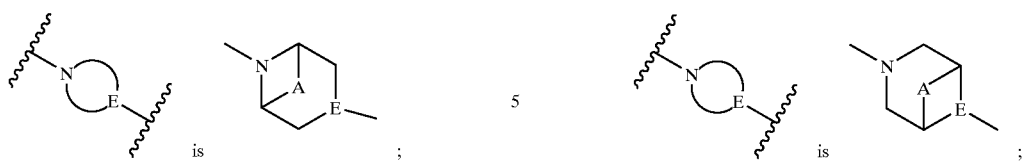

is ;

and E is C—H, may be prepared from (DI) via catalytic hydrogenation in the presence of an acid. Compounds of formula (DI) may be converted to compounds of (BI), wherein

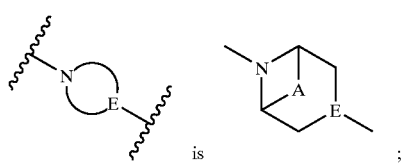

is ;

and E is C—O—($C_1$–$C_6$)alkyl, via alkylation of the hydroxyl group of the compound of formula (DI), by forming an anion at the hydroxy group using reagents such as alkyl lithium, alkyl potassium, alkyl sodium or alkylamine compounds in a solvent such as tetrahydrofuran or similar solvent or mixtures thereof at temperatures ranging from −20° C. to reflux temperature, then treating the reaction mixture with an alkylating agent, e.g., alkylhalide, etc. Similarly, compounds of formula (BI) wherein

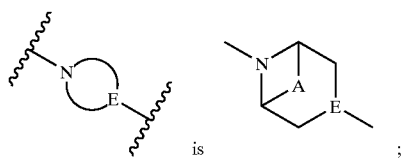

is ;

and E is CN, may be prepared by forming a leaving group at the hydroxy group of (DI) using reagents such as HBr or alkyl sulfonyl chloride in the presence of an acid acceptor, in a solvent such as benzene, a chlorinated solvent, or a lower alkyl (e.g., ($C_1$–$C_6$)alkyl) ether at temperatures ranging from −20° C. to solvent reflux temperature, followed by treatment of the reaction mixture with a cyanide salt, e.g., lithium cyanide, potassium cyanide, sodium cyanide, tetrabutylammonium cyanide, etc., in a solvent such as a lower alkyl (e.g., ($C_1$–$C_6$)alkyl) alcohol, dimethyl formamide, dimethyl acetamide at temperatures ranging from ambient to solvent reflux temperature.

Protecting groups on the nitrogen atoms of compounds (EIB) and (DI) are any of those protecting groups commonly known and used for such reactions, including, e.g., benzyl, benzyloxycarbonyl, t-butoxycarbonyl, trityl groups, etc. It is often convenient to remove such groups by readily practiced hydrogenation or acidic procedures readily known in the art as set forth in Greene and Wuts, *Protective Groups in Organic Synthesis* (John Wiley & Sons, New York, 1991).

may be formed in accordance with Scheme II-B.

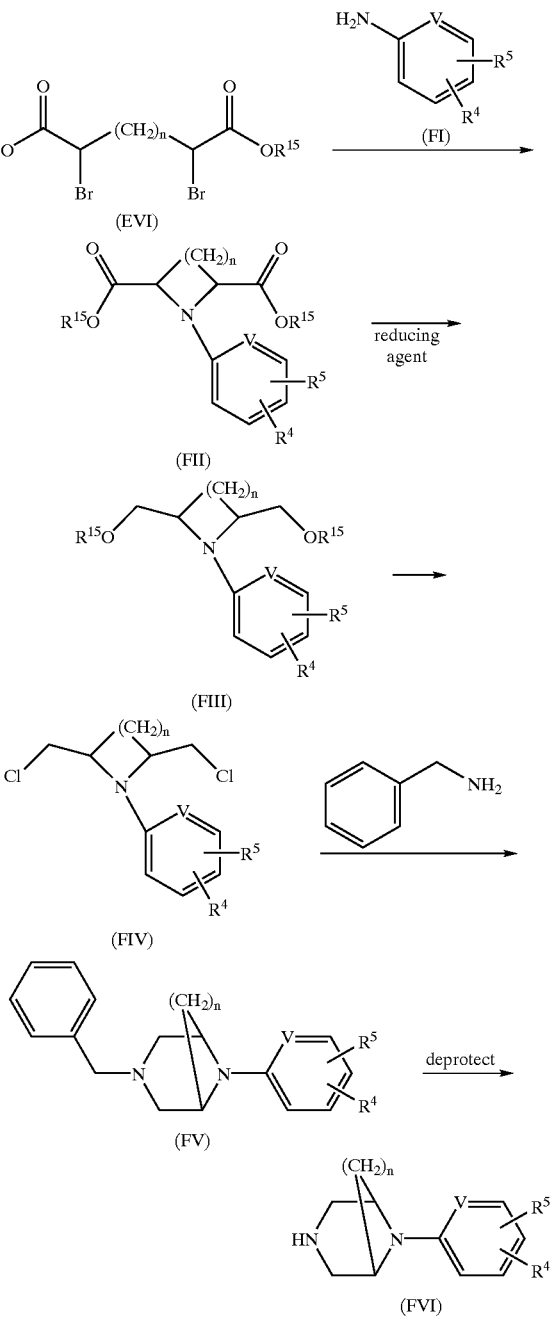

Referring to Scheme II-B, a compound of general formula (EVI), wherein $R^{15}$ is H or ($C_1$–$C_6$)alkyl, and n is 1 or 2, is allowed to react with an aryl amine of formula (FI) wherein V, $R^4$ and $R^5$ are as defined above in presence of a base, such as triethylamine, potassium carbonate, etc., at a temperature ranging from ambient temperature to the reflux temperature of a solvent or a mixture of solvents selected from the group consisting of dimethylformamide, acetonitrile, chloroform, dioxane, acetone, water, or lower alcohols (e.g., propanol, ethanol, methanol, etc.) to provide a compound of general formula (FII).

The compound of general formula (FII) formed in the first step is then transformed into the protected diol derivative of the formula (FIII) in the presence of a reducing agent, such as, e.g., an aluminum hydride or a borohydride, at a temperature ranging from ambient temperature to the reflux temperature of a solvent or a mixture of solvents selected from the group consisting of lower alkyl (e.g., ($C_1$–$C_6$)alkyl) alcohols, lower cyclic or acyclic alkyl ethers or dioxane. The compound of formula (FIII) is then converted into a dichloride compound of formula (FIV) by treating the compound of formula (FIII) with a reagent, such as, e.g., $SO_2Cl_2$, $POCl_3$ or similar chlorinating reagents, in the absence or presence of a solvent, such as, e.g., chloroform, carbon tetrachloride or methylene chloride at a temperatures ranging from ambient temperature to the reflux temperature of any one of said solvents or mixtures thereof. The compound of formula (FIV) is then converted to a compound of formula (FV) by reacting a compound with Formula (FIV) with an excess of benzylamine, in the absence or presence of a solvent, or mixture of solvents, selected from dimethyl formamide, dioxane, N,N-dimethylacetamide or pyrrolidinone at a temperature ranging from room temperature to the reflux temperature of any of those solvents or mixtures thereof. Finally, the compound of general formula (FV) is then transformed to a compound of general formula (FVI) (i.e., a compound of formula (BI) wherein

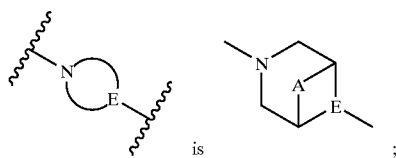

is ;

E is N, and n is 1 or 2) by removing the benzyl grouping using hydrogen gas in presence of a catalyst selected from the group consisting of palladium on carbon, platinum oxide or similar reagents in a solvent or mixture of solvents selected from the group consisting of lower cyclic or acyclic alkyl alcohols, lower cyclic or acyclic alkyl ethers, water, acetic acid, formic acid, hydrochloric acid or dimethyl formamide, at a temperature ranging from ambient temperature to the reflux temperatures of said solvent or mixture of solvents, at a hydrogen gas pressure ranging from 0 to 5 atmospheres. Compounds of general formula (FVI) are converted into compounds of general formula (I) using procedures which are essentially identically as those described in Scheme I.

Compounds of formula (BI) wherein

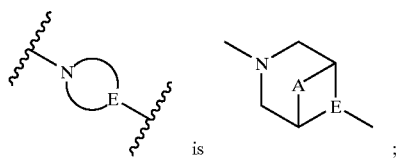

is ;

E is CH, C—CN, C—($C_1$–$C_6$)alkyl, etc. may be prepared using procedures similar to those described in International Patent Publication No. WO 00/32600, which is drawn to the preparation of 8-azabicyclo[3.2.1]oct-2-ene and -octane derivatives, or alternatively, using procedures similar to those described in Husbands et al., *J. Org. Chem.*, 63(3), pp. 418–419 (1998), and Portoghese et al. in *J. Med. Chem.*, 11(2), pp. 219–25 (1968) describing the synthesis of ring-constrained analogs of meperidine. All of the foregoing references are hereby incorporated by reference.

Compounds of formula (BI) wherein

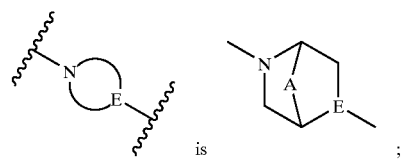

is ;

may be made in accordance with Scheme II-C below.

Referring to Scheme II-C, a compound of general formula (GI-A) or (G1-B) wherein, in each, X is halo (Cl, Br, or I), is allowed to react with an aryl amine of formula (FI), wherein V, $R^4$ and $R^5$ are as defined, above in the presence of a base, such as triethylamine, potassium carbonate, etc., at a temperature ranging from ambient to the reflux temperature of the solvent or a mixture of solvents selected from the group consisting of glyme, diglyme, dimethylformamide, acetonitrile, chloroform, dioxane, acetone, water or lower alcohols (e.g., propanol, ethanol, methanol, etc.) to provide a compound of general formula (GII-A) or (GII-B), respectively. Other appropriately substituted benzyl groups may be used in place of the benzyl group depicted in Scheme II-C. Using this procedure a mixture of compounds of formula (GII-A) or (GII-B) has been formed under comparable conditions from the compound of formula (GI-A) alone. This mixture of isomers may be separated from via chromatographic techniques, such as silica gel flash chromatography using a polar gradient of solvents.

The compounds of formulae (GII-A) and (GII-B) may be transformed to their free base compounds by removing the benzyl group using hydrogen gas in presence of a catalyst selected from the group consisting of palladium on carbon, platinum oxide or similar reagents in a solvent or mixture of solvents selected from the group consisting of lower cyclic or acyclic alkyl alcohols, lower cyclic or acyclic alkyl ethers, water, acetic acid, formic acid, hydrochloric acid or dimethyl formamide, at a temperature ranging from ambient temperature to the reflux temperatures of said solvent or mixture of solvents, at a hydrogen gas pressure ranging from 0 to 5 atmospheres. Compounds of general formula (GIIIA) and (GIIIB) are converted into compounds of general formula (I) using procedures which are essentially identically as those described in Scheme I.

Scheme II-C

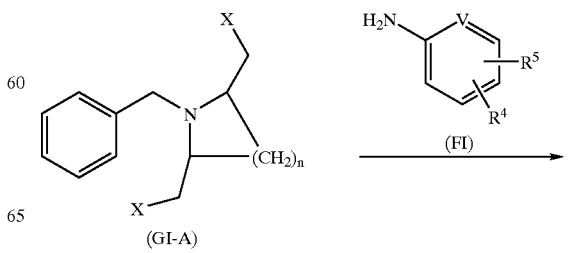

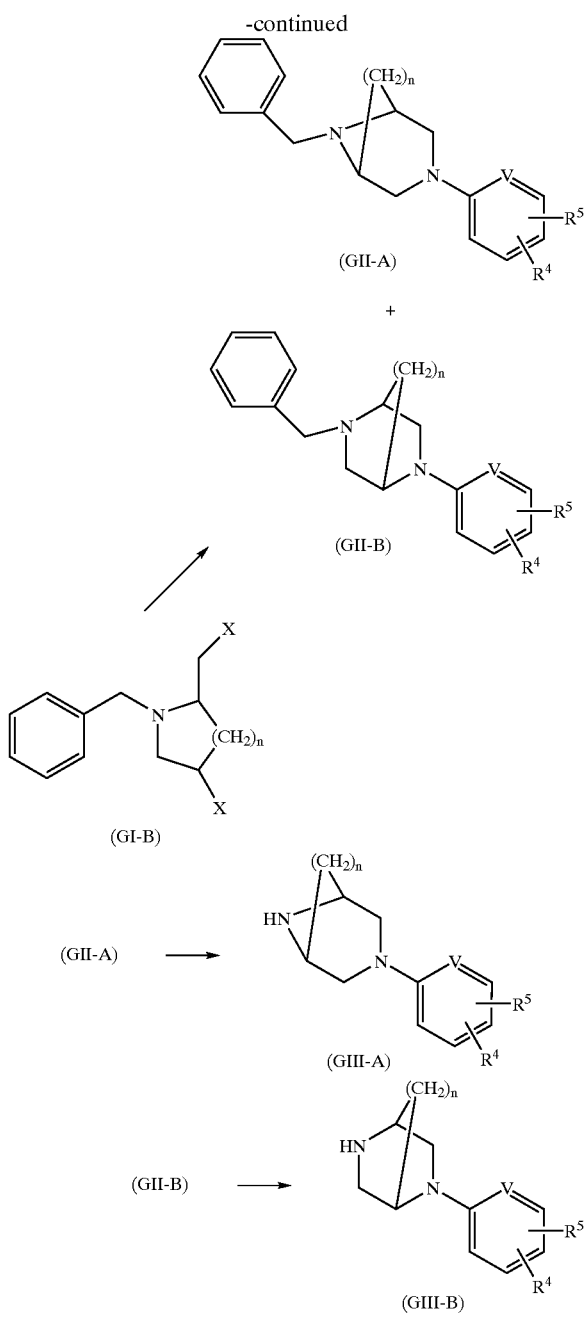

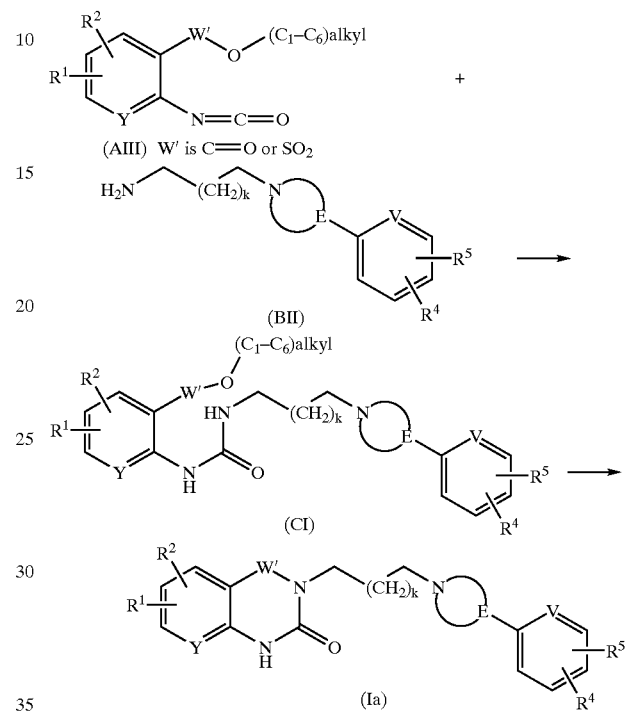

Compounds of formula (BI) where

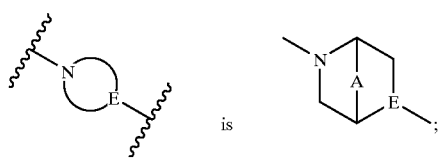

and E is CH, C—CN, C—($C_1$–$C_6$)alkyl may be prepared by procedures similar to those described in German Patent publication No. DE 2,749,584, which is drawn to the preparation of bridged geminal diphenylpiperidines; those in International Patent Publication No. WO 00/32600, which is drawn to the preparation of 8-azabicyclo[3.2.1]oct-2-ene and -octane derivatives; and those in Husbands et. al., *J.*

*Org. Chem.*, 63(3), 418–419 (1998), which is drawn to the synthesis of ring-constrained analogs of meperidine. All of the foregoing references are hereby incorporated by reference.

Further specific embodiments of the invention may also be prepared in accordance with reaction Scheme III.

In Scheme III, a compound of formula (Ia), wherein the difference with compounds of formula (I) is that W' is C═O or $SO_2$ and U is NH; may be prepared by allowing a compound of the general formula (AIII), wherein Y, $R^1$ and $R^2$ are as defined above; to react with a compound of the general formula (BII), wherein

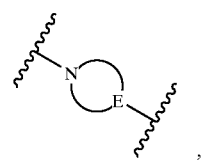

k, A, E, V, $R^4$ and $R^5$ are as defined above, to provide an intermediate compound of the general formula (CI). A compound of formula (Ia) is then formed via a ring closure of intermediate (CI), i.e., a cyclic urea formation to form the quinazoline ring. The steps of this reaction may be carried out in a solvent, such as, e.g., a lower alcohol, a cyclic or acyclic mono-/di-alkylamide, acetonitrile, a cyclic or acyclic alkyl ether, or an aromatic solvent (e.g., benzene, toluene, etc.), at a temperature in the range of 0° C. to 150° C. The intermediate compound (CI) may be isolated or further permitted to undergo the ring closure reaction in the same reaction vessel/mixture under similar conditions.

As shown in Scheme IV, below, compounds of the general formula (AIII) are, for example, prepared by reacting a compound of the general formula (DIII), where Y and W' are as defined above, with triphosgene, or an equivalent thereof, such as carbonyl diimidazole, phosgene or the like, in the presence of a base such as a tertiary amine in various combinations of inert organic solvents, e.g., cyclic and acyclic alkyl ethers, cyclic and acyclic alkyl esters, cyclic and acyclic alkyl ketones, pyridine derivatives and halogenated solvents. Reaction temperatures are preferably about 0° C. at the beginning of the reaction period, and then are gradually increase to the reflux temperature of the solvent combination used.

Scheme IV

As shown in Scheme V below, compounds of the general formula (BII) are, for example, prepared by reacting a compound of the general formula (BI) with an ω-aminoalkyl transferring agent of the general formula (EII), thereby providing compounds of the general formula (DII), from which the protecting groups may then removed so as to arrive at the compounds (BII). The coupling reaction is typically conducted in a solvent, such as, e.g., an alcohol, a cyclic or acyclic alkyl ester, a cyclic or acyclic alkyl ketone, a cyclic or acyclic mono- or dialkylamides, acetonitrile or a cyclic or bicyclic alkyl ethers, or combination of any of these solvents. The presence of an acid acceptor, e.g., an alkali carbonate or tertiary amine, is often useful to promote the reaction. When protecting groups, such as benzyl, benzyloxycarbonyl, t-butoxycarbonyl, or trityl groups are employed, it is often convenient to remove such groups using readily practiced hydrogenation or acidic procedures; other commonly used protecting groups are also introduced and removed using well known, and readily practiced, techniques, such as those set forth in Greene et al., supra.

Scheme V

Suitable leaving groups are those leaving groups that would be well known to one of skill in the art, e.g., a tosylate group, mesylate group, etc.

Another further method for preparing compounds of formula (I) is set forth in Scheme VI below. In Scheme VI, the compound of formula (Ib) differs from the compounds of general formula (I) in that W is C(O), and U is $NH_2$.

Scheme VI

Compounds of formula (Ib) may be prepared by reacting a compound of formula (DIII') via reaction with a halo ($C_3$–$C_4$)alkylisocyanate, e.g., chloropropylisocyanate, chlorobutylisocyanate, etc., to arrive at the corresponding ureido compound (GI') which is then further reacted, either after isolation or in the same reaction mixture, with a base or acid acceptor to form the tricyclic compound (FI). The tricyclic (FI) compound is then converted to a compound of formula (Ib) via heating with a compound of formula (BI), or salt thereof, e.g., the hydrochloride salt, etc. The steps of reaction Scheme VI may be all be conducted in the presence of an acid acceptor, e.g., an alkali carbonate, bicarbonate, or tertiary amine, etc. in a solvent system such as that described above for Scheme IV.

The preparation of other compounds of formula (I) not specifically described in the foregoing section can be accomplished using combinations of the reactions described above that will be apparent to those skilled in the art. Furthermore, in each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred, as a matter of convenience.

Those compounds of the invention which are basic in nature are capable of forming a wide variety of different salts with various inorganic and organic acids. Although such salts must be pharmaceutically acceptable for administration to animals, it is often desirable in practice to initially isolate the compound of formula (I) from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids used to prepare the pharmaceutically acceptable acid addition salts of the basic compounds of this invention are those which form non-toxic acid addition salts, i.e., salts containing pharmaceutically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate (i.e., 1,1'-methylene-bis-(2-hydroxy-3-naphthoate)) salts.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention. Although such salts must be pharmaceutically acceptable for administration to animals, it is often desirable in practice to initially isolate a compound of the formula (I) from the reaction mixture as a pharmaceutically unacceptable salt, convert the latter back to the free base compound by treatment with an alkaline reagent, and subsequently convert the latter free base to a pharmaceutically acceptable acid addition salt. Such salts are readily prepared by treating the base compound with a substantially equivalent amount of the chosen mineral or organic acid in an aqueous solvent medium, or in a suitable organic solvent, such as methanol or ethanol. Upon careful evaporation of the solvent, the desired solid salt is readily obtained.

The compounds of this invention and their pharmaceutically acceptable salts are useful as selective serotonin reuptake inhibitors and 5-$HT_{2A}$ receptor binding inhibitors. Therefore, said compounds are able to function as therapeutic agents in mammals, including humans, afflicted with various diseases, disorders and conditions, such as those set forth above, characterized by aberrant behavior of the serotonin neurotransmission system.

Serotonin receptor binding affinities of compounds of formula (I) can be determined using standard radioligand binding assays as described in the literature. For example, 5-$HT_{1A}$ receptor binding affinities can be measured using the procedure of Hoyer et al. (*Brain Res.*, 376, 85 (1986)), and 5-$HT_{1D}$ binding affinities can be measured using the procedure of Heuring and Peroutka (*J. Neurosci.*, 7, 894 (1987)); the contents of these documents are incorporated herein by reference.

In vitro binding activity at the 5-$HT_{1D}$ receptor binding site is, for example, determined according to the following procedure. Bovine caudate tissue is homogenized and suspended in 20 volumes of a buffer containing 50 mM TRIS-HCl (tris[hydroxymethyl]aminomethane hydrochloride) at a pH of 7.7, following which the homogenate is centrifuged at 45,000 g for 10 minutes. The resulting supernatant is discarded, and the pellet is resuspended in approximately 20 volumes of 50 mM TRIS-HCl buffer at pH 7.7; said suspension is pre-incubated for 15 minutes at 37° C., after which it is centrifuged again at 45,000 G for 10 minutes. The resulting supernatant discarded, and the pellet (approximately 1 gram) is resuspended in 150 ml of a buffer of 15 mM TRIS-HCl containing 0.01 percent ascorbic acid, final pH 7.7, 10 $\mu$M pargyline and 4 mM calcium chloride ($CaCl_2$)—the suspension is kept on ice at least 30 minutes prior to use.

The inhibitor, control or vehicle is incubated according to the following procedure: to 50 $\mu$l of a 20 percent dimethylsulfoxide (DMSO)/80 percent distilled water solution is added 200 $\mu$l of tritiated 5-hydroxytryptamine (2 nM) in a buffer of 50 mM TRIS-HCl containing 0.01 percent ascorbic acid at pH 7.7, 10 $\mu$M pargyline, 4 mM calcium chloride, 100 nM of 8-hydroxy-DPAT (dipropylaminotetraline) and 100 nM of mesulergine. To this mixture is added 750 $\mu$l of bovine caudate tissue, and the resulting suspension is vortexed to ensure a homogenous suspension; the suspension is then incubated in a shaking water bath for 30 minutes at 25° C.; after incubation is complete, the suspension is filtered using glass fiber filters (e.g., Whatman GF/B-filters). The pellet is washed three times with 4 ml of a buffer of 50 mM TRIS-HCl (pH 7.7), and is then placed in a scintillation vial with 5 ml of scintillation fluid (aquasol 2) and allowed to sit overnight. The percent inhibition is calculated for each dose of the compound, and an $IC_{50}$ value is then calculated from the percent inhibition values.

Binding affinities at the 5-$HT_{1A}$ receptor is, for example, determined according to the following procedure. Rat brain cortex tissue is homogenized and divided into samples of 1 g lots and diluted with 10 volumes of 0.32 M sucrose solution. The suspension is then centrifuged at 900 g for 10 minutes, the supernatant separated and recentrifuged at 70,000 g for 15 minutes and the pellets are then collected and resuspended in 10 volumes of 15 mM TRIS-HCl (pH 7.5); the remaining supernatant is discarded. The resulting suspension is allowed to incubate for 15 minutes at 37° C., after which it is then centrifuged at 70,000 g for 15 minutes and the supernatant discarded. The resulting tissue pellet is resuspended in a buffer of 50 mM TRIS-HCl (pH 7.7) containing 4 mM of calcium chloride and 0.01 percent ascorbic acid—this tissue suspension is stored at −70° C. until ready for an experiment.

The tissue can be thawed immediately prior to use, diluted with 10 $\mu$M pargyline and kept on ice; tissue incubation is according to the following procedure. Fifty microliters of control, inhibitor, or vehicle (1 percent DMSO final concentration) is prepared at various dosages. To this solution is added 200 $\mu$l of tritiated 8-hydroxy DPAT at a concentration of 1.5 nM in a buffer of 50 mM TRIS-HCl at pH 7.7, containing 4 mM calcium chloride, 0.01 percent ascorbic acid and pargyline. 750 µl of tissue is added, the resulting suspension is vortexed to ensure homogeneity, and is then incubated in a shaking water bath for 30 minutes at 37° C. The solution is filtered, and then washed twice with 4 ml of 10 mM TRIS-HCl at pH 7.5 containing 154 mM of sodium chloride.

Agonist and antagonist activities of compounds of formulae (I) at the $5\text{-HT}_{1A}$ and $5\text{-HT}_{1D}$ receptors is, for example, determined using a single saturating concentration according to the following procedure. Male Hartley guinea pigs are decapitated and $5\text{-HT}_{1A}$ receptors are dissected out of the hippocampus, while $5\text{-HT}_{1D}$ receptors are obtained by slicing at 350 mm on a McIlwain tissue chopper and dissecting out the substantia nigra from the appropriate slices. The individual tissues are homogenized in a 5 mM HEPES buffer containing 1 mM EGTA (pH 7.5) using a hand-held glass-Teflon® homogenizer and centrifuged at 35,000 g for 10 minutes at 4° C. The resulting pellets are resuspended in a 100 mM HEPES buffer containing 1 mM EGTA (pH 7.5), to a final protein concentration of 20 mg (hippocampus) or 5 mg (substantia nigra) of protein per tube; the following agents are added so that the reaction mix in each tube contains 2.0 mM $MgCl_2$, 0.5 mM ATP, 1.0 mM cAMP, 0.5 mM IBMX, 10 mM phosphocreatine, 0.31 mg/mL creatine phosphokinase, 100 µM GTP and 0.5–1 microcuries of $[^{32}P]$-ATP (30 Ci/mmol: NEG-003—New England Nuclear). Incubation is initiated by the addition of tissue to siliconized microfuge tubes (in triplicate) at 30° C. for 15 minutes. Each tube receives 20 µl tissue, 10 µl drug or buffer (at 10× final concentration), 10 µl of 32 nM agonist or buffer (at 10× final concentration), 20 µl forskolin (3 µM final concentration) and 40 µl of the preceding reaction mix. Incubation is terminated by the addition of 100 µl 2% SDS, 1.3 mM cAMP, 45 mM ATP solution containing 40,000 dpm $[^{3}H]$-cAMP (30 Ci/mmol: NET-275—New England Nuclear) to monitor the recovery of cAMP from the columns (the separation of $[^{32}P]$-ATP and $[^{32}P]$-cAMP is accomplished using the method of Salomon et al., *Analytical Biochemistry*, 1974, 58, 541–548, the contents of which are incorporated herein by reference). Radioactivity is quantified by liquid scintillation counting. Maximal inhibition is defined by 10 µM (R)-8-OH-DPAT for $5\text{-HT}_{1A}$ receptors, and 320 nM 5-HT for $5\text{-HT}_{1D}$ receptors. Percent inhibitions by the test compounds are then calculated in relation to the inhibitory effect of (R)-8-OH-DPAT for $5\text{-HT}_{1A}$ receptors or 5-HT for $5\text{-HT}_{1D}$ receptors. The reversal of agonist-induced inhibition of forskolin-stimulated adenylate cyclase activity is calculated in relation to the 32 nM agonist effect.

The compounds of this invention are, for example, tested for in vivo activity for antagonism of $5\text{-HT}_{1D}$ agonist-induced hypothermia in guinea pigs according to the following procedure. Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing. Compounds of formula (I) are administered, for example, as solutions in a volume of 1 ml/kg; the vehicle used is varied depending on compound solubility. Test compounds are typically administered either sixty minutes orally (p.o.) or 0 minutes subcutaneously (s.c.) prior to administration of a $5\text{-HT}_{1D}$ agonist, such as [3-(1-methylpyrrolidin-2-ylmethyl)-1H-indol-5-yl]-(3-nitropyridin-3-yl)-amine, which can be prepared as described in PCT publication WO93/111 06, published Jun. 10, 1993 (the contents of which are incorporated herein by reference), and which is administered at a dose of 5.6 mg/kg, s.c.

Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The $5\text{-HT}_{1D}$ agonist is then administered at 0 minutes and temperatures are taken 30, 60, 120 and 240 minutes later. In subcutaneous screening experiments, a pre-drug baseline temperature reading is made at −30 minutes. The test compound and $5\text{-HT}_{1D}$ agonists are given concurrently and temperatures are taken at 30, 60, 120 and 240 minutes later. Data are analyzed with two-way analysis of variants with repeated measures in Newman-Keuls post hoc analysis.

The serotonin $5\text{-HT}_1$ agonist activity can be determined by in vitro receptor binding assay, as described for the $5\text{-HT}_{1A}$ receptor using rat cortex as the receptor source and $[^{3}H]$-8-OH-DPAT as the radioligand [D. Hoyer et al. *Eur. J. Pharm.*, 118, 13 (1985)] and as described for the $5\text{-HT}_{1D}$ receptor using bovine caudate as the receptor source and $[^{3}H]$serotonin as the radioligand [R. E. Heuring and S. J. Peroutka, *J. Neuroscience*, 7, 894 (1987)]; the contents of these documents are incorporated herein by reference.

The binding activity at the $5\text{-HT}_{2A}$ receptor is, for example, determined according to the following procedure. Male Sprague-Dawley rats are decapitated and their brains removed. Frontal cortices are dissected and homogenized in 50 mM Tris HCl buffer (pH 7.4 at 4° C.) containing 2 mM MgCl2 using a Polytron homogenizer (setting 15,000 rpm). The homogenate is centrifuged for ten minutes at 40,000×g (20,000 rpm in a Sorvall SS34 rotor). The supernatant was discarded and the pellet resuspended with the Polytron homogenizer in fresh ice-cold 50 mM TRIS HCl (pH 7.4 at 4° C.) buffer containing 2 mM MgCl2 and centrifuged again. The final pellet was resuspended in 50 mM Tris HCl buffer (pH 7.7 at 22° C.) for a final tissue concentration of 9 mgs wet weight tissue per mL buffer. Incubation is initiated by the addition of tissue to V-bottom polypropylene 96 well plates (in triplicate). Incubation is at 37° C. for 15 minutes in a water bath. Each tube receives 200 µL tissue suspension, 25 µL $^{3}$H-ketanserin (0.4 nM final concentration), and 25 µL drug or buffer. Nonspecific binding is determined using 10 µM cinanserin. Incubation is ended by rapid filtration under vacuum through fire-treated Whatman GF/B glass fiber filters (presoaked in 0.5% polyethenylenimine (PEI) and dried) and rinsed with ice-cold 50 mM Tris HCl buffer (pH 7.7 at 4° C.), setting 555 on a Skatron 96 well harvester. Filters are put into sample bags with 10 mL Betaplate scintillation fluid and allowed to sit 10 minutes before counting on a Betaplate scintillation counter (Wallac).

The binding activity at the $\alpha_1$ receptor is, for example, determined according to the following procedure. Male Sprague-Dawley rats are decapitated and their brains removed. Cortices are dissected and homogenized in 50 mM Tris HCl buffer (pH 7.4 at 4° C.) containing 2 mM MgCl2 using a Polytron homogenizer (setting 15,000 rpm). The homogenate is centrifuged for ten minutes at 40,000×g (20,000 rpm in Sorvall SS34 rotor). The supernatant was discarded and the pellet resuspended with the Polytron homogenizer in fresh ice-cold 50 mM TRIS HCl (pH 7.4 at 4° C.) buffer containing 2 mM $MgCl_2$ and centrifuged again. The final pellet was resuspended in 50 mM Tris HCl buffer (pH 8.0 at 22° C.) for a final tissue concentration of 12.5 mgs wet weight tissue per mL buffer. Incubation is initiated by the addition of tissue to V-bottom polypropylene 96 well plates (in triplicate). Incubation is at 25° C. for 30 minutes on a shaker. Each tube receives 200 µL tissue suspension, 25 µL 3H-Prazosin (0.2 nM final concentration) and 25 µL drug or buffer. Nonspecific binding is determined using 10 µM phentolamine. Incubation is ended by rapid filtration under vacuum through fire-treated Whatman GF/B glass fiber filters (presoaked in 0.5% PEI and dried) and rinsed with ice-cold 50 mM Tris HCl buffer (pH 7.7 at 4° C.), setting 555 on a Skatron 96 well harvester. Filters are put into sample bags with 10 mL Betaplate scintillation fluid and allowed to sit 10 minutes before counting on a Betaplate scintillation counter (Wallac).

The binding activity at the dopamine $D_2$ receptor is, for example, determined according to the following procedure. Male Sprague-Dawley rats are decapitated and their brains removed. Striata are dissected and homogenized in 50 mM Tris HCl buffer (pH 7.4 at 4° C.) containing 2 mM $MgCl_2$ using a Polytron homogenizer (setting 15,000 rpm). The homogenate is centrifuged for ten minutes at 40,000×g (20,000 rpm in a Sorvall SS34 rotor). The supernatant was discarded and the pellet resuspended with the Polytron in fresh ice-cold 50 mM Tris HCl (pH 7.4 at 4° C.) containing 2 mM $MgCl_2$ buffer and centrifuged again. The final pellet was resuspended in 50 mM Tris HCl buffer containing 100 mM NaCl, 1 mM $MgCl_2$ (pH 7.4 at 37° C.) for a final tissue concentration of 3 mg wet weight tissue per mL buffer. Incubation is initiated by the addition of tissue to V-bottom polypropylene 96 well plates (in duplicate or triplicate). Incubation is at 37° C. for 15 minutes in a heated water bath. Each tube receives 200 µL tissue suspension, 25 µL $^3$H-spiperone (0.2 nM final concentration) and 25 µL drug or buffer. Nonspecific binding is determined using 10 µM (+)-butaclamol. Incubation is ended by rapid filtration under vacuum through fire-treated Whatman GF/B glass fiber filters (presoaked in 0.5% PEI and dried) and rinsed with ice-cold 50 mM Tris HCl buffer (pH 7.7 at 4° C.), setting 555 on the Skatron 96 well harvester (15 sec wash). Filters are dried, put into sample bags with 10 mL Betaplate scintillation fluid and counted on a Betaplate scintillation counter (EG&G/Wallac).

The neurotransmitter uptake activity in rat synaptosomes or HEK-293 cells transfected with the human serotonin, dopamine or norepinephrine transporter is, for example, determined according to the following procedure. For rat synaptosomes preparation, male Sprague Dawley rats are decapitated and the brains removed. The cortex, hippocampi and corpus striata are dissected out and placed in ice cold sucrose buffer, 1 gram in 20 mls (320 mM sucrose containing 1 mg/ml glucose, 0.1 mM EDTA and brought up to pH 7.4 with Tris base). The tissues are homogenized in a glass homogenizing tube with a teflon pestle at 350 RPMS using a Potters homogenizer. The homogenate is centrifuged at 1000×g for 10 min, at 4 C. The resulting supernatant is re-centrifuged at 17,000×g for 20 min, at 4 C. The final pellet is then resuspended in an appropriate volume of sucrose buffer that yielded less than 10% uptake.

For cell preparation, HEK-293 cells transfected with the human serotonin (5-HT), norepinephrine (NE) or dopamine (DA) transporter were grown in DMEM (Gibco) supplemented with 10% dialyzed FBS (Gibco), 2 mM L-glutamine and 250 µg/ml G418 for the 5-HT and NE transporter or 2 µg/ml puromycin for the DA transporter, for selection pressure. The cells were grown in Gibco triple flasks, harvested with PBS and diluted to an appropriate amount to yield less than 10% uptake.

For the neurotransmitter uptake assay, the uptake assays were conducted in glass tubes containing 50 µL of solvent, inhibitor or 10 µM sertraline, desipramine or nomifensine for the 5-HT, NE or DA assay nonspecific uptake, respectively. Each tube contained 400 µL of [$^3$H]5-HT (5 nM final), [$^3$H]NE (20 nM final) or [$^3$H]DA (5 nM final) made up in modified Krebs containing 100 µM pargyline and glucose (1 mg/ml). The tubes were placed on ice, 50 µL of synaptosomes or cells was added to each tube. The tubes were then incubated at 37C. for the 7 minutes (5-HT, DA) or 10 minutes (NE). The incubation was terminated by filtration (GF/B filters), using a 96 well Brandel Cell Harvester, the filters were washed with modified Krebs buffer and either counted in a liquid scintillation counter or in a LKB Beta Plate counter.

Compounds prepared as working examples of the present invention and tested in accordance with the foregoing methods showed good binding activity in the range of more than 50% inhibition at <50 (fifty) nM concentration in the serotonin reuptake assay and binding assays for 5-$HT_{2A}$ serotonin receptor while having an affinity of >100 (one hundred) nM at the dopamine D2 receptor, 5-$HT_{1A}$ serotonin, 5-$HT_{1D}$ or $α_1$ adrenergic receptor.

The compounds of this invention, and their pharmaceutically acceptable salts, can be administered via either the oral, parenteral or topical routes. In general, these compounds are most desirably administered in dosages ranging from about 0.01 to about 250 mg per day, in single or divided doses (e.g., from 1 to 4 doses per day), although variations will necessarily occur depending upon the species, weight and condition of the subject being treated, as well as the particular route of administration chosen. However, a dosage level that is in the range of about 0.07 mg to about 21 mg per kg of body weight per day is most desirably employed. Variations may nevertheless occur depending upon the subject being treated and its individual response to said medicament, as well as on the type of pharmaceutical formulation chosen, and the time period, and interval, at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants, such as starch (and preferably corn, potato or tapioca starch), alginic acid and certain complex silicates, and granulation binders, such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of formula (I) or II in either sesame or peanut oil, or in aqueous propylene glycol, may be employed. The aqueous solutions should be suitably buffered (preferably at a pH of greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically for the treatment of conditions of the skin; this may be done by way of creams, jellies, gels, pastes, patches, ointments and the like, in accordance with standard pharmaceutical practice.

EXAMPLES

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra were measured using standard techniques. The peak shapes are denoted as follows: s, singlet; d, doublet; t, triplet; q, quartet, m, multiplet, b, broad.

Example 1

2,2,2-TRIFLUORO-N-(3-HYDROXYPROPYL)-ACETAMIDE

3-Amino-1-propanol (10.0 mL, 0.131 mol) and methyl trifluoroacetate (65 mL, 0.646 mol) in methanol (200 mL) were refluxed for 1.5 hours, cooled and concentrated to give 2,2,2-trifluoro-N-(3-hydroxypropyl)-acetamide (22.87 g, quantitative) as a light yellow oil which was used without purification. NMR CDCl$_3$ δ7.45 (br s, 1H), 3.77 (t, J=5.5 Hz, 2H), 3.53–3.42 (m, 2H), 2.45 (s, 1H), 1.83–1.75 (m, 2H).

Example 2

METHANESULFONIC ACID 3-(2,2,2-TRIFLUOROACETYLAMINO)-PROPYL ESTER

A solution of 2,2,2-trifluoro-N-(3-hydroxypropyl)-acetamide (2.00 g, 11.69 mmol) and triethylamine (1.7 mL, 12.2 mmol) in methylene chloride (35 mL) was cooled in an ice bath and methanesulfonic acid anhydride in methylene chloride (15 mL) was added dropwise over 1 minute. After stirring for 45 minutes. at 0° C. the reaction was concentrated, the residue was partitioned between ether and water, the organic extractions were washed with brine and dried over magnesium sulfate. Concentration yielded methanesulfonic acid 3-(2,2,2-trifluoroacetylamino)-propyl ester

Example 3

3-(2,4-DIOXO-1,4-DIHYDRO-2H-QUINAZOLIN-3-YL)PROPIONALDEHYDE

Benzoylene urea (4.0 9, 24.7 mmol), Triton B (40 wt % in methanol) (11.0 mL, 24.7 mmol), water (80 mL) and methanol (400 mL) were combined at ambient temperature and stirred vigorously for 15 minutes. (until all the solids had gone into solution). To this colorless solution, acrolein (1.7 mL, 24.7 mmol) in methanol (20 mL) was added dropwise over 5 minutes. to give a yellow solution. The reaction was then heated to 55° C. and stirred for 2 hours. and then at room temperature for approximately 16 hours. The yellow solution was concentrated to give a yellow oil which was taken up in ethyl acetate (25 mL) and water (50 mL). The aqueous layer was extracted again with ethyl acetate (25 mL). The organic layers were combined, washed with 1N HCl (20 mL), water (20 mL), saturated sodium bicarbonate solution (20 mL) and brine (20 mL), the organic layer was dried over magnesium sulfate and concentrated to give 3-[2,4-dioxo-1,4-dihydro-2H-quinazolin-3-yl] propionaldehyde as a yellow foam (3.2 g, 59%) which was used without further purification. The NMR data showed a purity of ~70%. NMR CDCl$_3$ δ9.85 (s, 1H), 8.10–8.06 (m, 1H), 7.63–7.57 (m, 1H), 7.24–7.19 (m, 1H), 7.13–7.07 (m, 1H), 4.44–4.40 (m, 2H), 2.85 (dt, 2H, $J_{1,2}$=2 Hz, $J_{1,3}$=7 Hz); MS=219 (p+1).

Example 4

2-[3-(2-[1,3]DIOXOLAN-2-YL-ETHYL)-UREIDO]-BENZOIC ACID METHYL ESTER

Methylanthranilate (1.18 g, 7.79 mmol) and triethylamine (2.5 mL, 17.7 mmol) in methylene chloride (10 mL) were cooled in an ice bath. Triphosgene (0.69 g, 2.34 mmol) in methylene chloride (10 ml) was added dropwise over 10 minutes. and the resulting mixture was stirred for 1 hour at 0° C. to form the isocyanate intermediate. 2-(2-Aminoethyl)-1,3-dioxolane(2.00 g, 17.1 mmol) in methylene chloride (10 ml) was added dropwise at 0° C. over 10 minutes., then the mixture was warmed to ambient temperature and stirred for 15 hours. Concentration yielded a yellow solid which was taken up in ethyl acetate and sat. sodium bicarbonate solution; the layers were separated. The organic layer was washed with brine, dried over magnesium sulfate. Concentration yielded 2-[3-(2-[1,3]dioxolan-2-yl-ethyl)-ureido]-benzoic acid methyl ester (1.26 g, 60%) as a white solid. $^1$H NMR CDCl$_3$ δ10.26 (brd s, 1H), 8.51–8.44 (m, 1H), 7.95 (dd, J=2, 8 Hz, 1H), 7.49–7.44 (m, 1H), 6.95–6.91 (m, 1H), 5.35–5.10(brd s, 1H), 4.95 (t, J=4 Hz, 1H), 4.01–3.98 (m, 2H), 3.88 (S, 3H), 3.87–3.82 (m, 2H), 3.44 (t, J=6 Hz, 2H), 1.96–1.92 (m, 2H).

Example 5

3-(2-[1,3]DIOXOLAN-2-YL-ETHYL)-1H-QUINAZOLINE-2,4-DIONE

A white mixture of 2-[3-(2-[1,3]dioxolan-2-yl-ethyl)-ureido]-benzoic acid methyl ester (0.50 g, 1.70 mmol) and 1N sodium hydroxide (2.0 mL) in ethanol (10 mL) was warmed until all the solids had gone into solution. The resulting colorless solution was cooled to ambient temperature and stirred for 30 minutes. Concentration yielded a colorless foam which was dissolved in water (15 mL); after 15 minutes, a white crystalline solid formed. The white crystalline solid was collected and dried to yield 3-(2-[1,3] dioxolan-2-yl-ethyl)-1H-quinazoline-2,4-dione (0.19 g, 43%). $^1$NMR CDCl$_3$ δ7.92 (dd, J=1, 8 Hz, 1H), 7.67–7.61 (m, 1H), 7.22–7.15 (m, 2H) 4.88 (t, J=4 Hz, 1H), 4.00 (t, J=7 Hz, 2H), 3.89–3.71 (m, 4H), 1.93–1.86 (m, 2H).

Example 6

3-(2,4-DIOXO-1,4-DIHYDRO-2H-QUINAZOLIN-3-YL)-PROPIONALDEHYDE

A solution of 3-(2-[1,3]dioxolan-2-yl-ethyl)-1H-quinazoline-2,4-dione (0.11 g, 0.43 mmol) 10% sulfuric acid (10 mL) and Acetone (10 mL) was stirred at ambient temperature for 24 hours. Concentration yielded 3-[2,4-dioxo-1,4-dihydro-2H-quinazolin-3-yl]propionaldehyde (0.09 g, 95%) as an off-white solid. $^1$H NMR CDCl$_3$ δ9.85 (s, 1H), 8.10–8.06 (m,1H), 7.63–7.57 (m, 1H), 7.24–7.19 (m, 1H), 7.13–7.07 (m, 1H), 4.44–4.40 (m, 2H), 2.85 (dt, 2H, $J_{1,2}$=2 Hz, $J_{1,3}$=7 Hz).

Example 7

3-CHLORO-2-[3-(3-CHLORO-PROPYL)-UREIDO]-BENZOIC ACID

A 250 mL round bottom flask is charged with 2-amino-3-chlorobenzoic acid (5.00 g, 29.1 mmol) and 100 mL of 5% aqueous KHCO$_3$. The slurry is cooled to 0° C., and 3-chloropropylisocyanate (6.0 mL, 58 mmol) is added. The mixture is then allowed to warm to room temperature over 16 hours. HPLC analysis shows some starting material remaining, so the solution is recooled to 0° C. and an additional portion of the isocyanate (3.0 mL, 29 mmol) is added. After 2 hours, the solution is acidified with 1 N HCl (ca. 40 mL), and the resulting yellow solid is filtered, rinsing with 1 N HCl. The resulting solid (35.5 g) is recrystallized from 80 mL of hot ethanol, to provide the product as a white solid: 4.22 g, 14.5 mmol, 50% yield. M.p. 124.4–124.8° C. $^1$H NMR (CD$_3$OD): 7.84 (d, J=8, 1H), 7.64 (d, J=8, 1H), 7.24 (t, J=8, 1H), 3.68 (t, J=7, 2H), 3.37 (t, J=6, 2H), 2.01 (m, 2H). MS (Cl): 289 (M–H, 100), 196 (M-ClCH$_2$CH$_2$CH$_2$NH, 25)

Example 8

8-CHLORO-3,4-DIHYDRO-2H-1-OXA4A,9-DIAZA-ANTHRACEN-10-ONE

A 250 mL round bottom flask is charged with 3-chloro-2-[3-(3-chloro-propyl)-ureido]-benzoic acid (3.40 g, 11.7 mmol) and 50 mL of 10% aqueous KHCO$_3$, and warmed to reflux for 1 hour. 50 mL of H$_2$O is added and the solution is allowed to cool to room temperature, then to 0° C. The resulting yellow solid is collected by filtration to provide 2.32 g of crude product, which is recrystallized from CH$_2$Cl$_2$-isopropyl ether to provide the product as a white solid: 1.10 g (4.6 mmol, 40% yield). M.p. 206.7–207.9° C. $^1$H NMR (CDCl$_3$): 8.09 (d, J=8, 1H), 7.77 (d, J=8, 1H), 7.24 (t, J=8, 1H), 4.54 (t, J=5, 2H), 4.14 (t, J=6, 2H), 2.32 (m, 2H); MS (Cl): 2.37 (M+H, 100).

Example 9

8-CHLORO-3,4-DIHYDRO-2H-1-OXA-4a,9-DIAZA-ANTHRACEN-10-ONE

A 250 mL round bottom flask is charged with 2-amino-3-chlorobenzoic acid (5.00 g, 29.1 mmol) and 40 mL of 10% aqueous KHCO$_3$. The slurry is cooled to 0° C., and 3-chloropropylisocyanate (5.25 mL, 51.2 mmol) is added. The reaction mixture is allowed to warm to room temperature over 3 hours, warmed to reflux for 2 hours, then stirred at room temperature for 16 hours. It is then diluted with 40 mL H$_2$O and cooled to 0° C. The product is collected by filtration to provide 5.68 g of a yellow solid. This material is purified by recrystallization: it is dissolved in a minimal volume of warm CH$_2$Cl$_2$ (ca. 10 mL), cooled to 0° C., and IPE (ca. 20 mL) added to the point of cloudiness; crystallization is allowed to proceed at that temperature for 1 hour. The resulting yellow solid is collected and dried to provide 3.87 g (16.3 mmol, 56% yield) of light yellow solid.

Example 10

8-CHLORO-3{3-[3-(4-CHLORO-PHENYL)-3,8-DIAZA-BICYCLO[3.2.1]OCT-8-YL]-PROPYL}-1H-QUINAZOLINE-2,4-DIONE

8-Chloro-3,4-dihydro-2H-1-oxa-4a,9-diaza-anthracen-10-one (6.18g, 26.02 mmol), 3-(4-Chloro-phenyl)-3,8-diaza-bicyclo[3.2.1] octane (HCl salt) (5.62 g, 21.68 mmol), triethylamine (3.6 ml, 26.02 mmol), p-toluene sulfonic acid (0.74 g, 3.90 mmol) were combined in dimethyl acetamide (38 ml) and heated at 120° C. for 15 hours. The reaction was cooled to room temperature, diluted with H$_2$O and filtered the tan precipitate. Dissolved the tan solid in chloroform (400 ml), dried over magnesium sulfate, and concentrated to an off-white solid. Silica gel flash chromatography using 5% methanol/chloroform as the eluent yielded 8-Chloro-3-{3-[3-(4-chloro-phenyl)-3,8-diaza-bicyclo[3.2.1]oct-8-yl]-propyl}-1H-quinazoline-2,4-dione (8.3 g, 83.3%) as an off-white solid; Mp. 194–196° C. Maleate salt was formed by dissolving the solid in chloroform (100 ml) and maleic acid (2.52 g, 1.2 eq) in ethyl acetate (20 ml) was added. The mix was concentrated and the off-white solid was washed with ethyl acetate to yield maleate salt (8.95 g). A portion was recrystallized from acetonitrile yielding off-white crystalline solid which had the following properties: Mp. 186–188° C.; $^1$H NMR DMSO-d$_6$ δ: 11.07 (brd s, 1H), 9.50 (brd s, 1H), 7.92 (dd, J=1.2, 6.6 Hz, 1H, 7.79 (dd, J=1.2, 6.6 Hz, 1H), 7.26–7.17 (m, 3H), 6.89 (d, J=9.1 Hz, 2H), 6.00 (s, 2H), 4.09 ( brd s, 2H), 3.99 (t, J=6.6 Hz, 2H), 3.70–3.65 (m, 2H), 3.17–2.98 (m, 4H), 2.20–2.00 (m, 4H), 1.95–1.86 (m, 2H). $^{13}$C NMR DMSO-d$_6$ δ: 167.87, 162.14, 150.76, 149.18, 137.06, 136.53, 129.338, 127.26, 123.85, 119.35, 116.84, 116.63, 61.11, 52.08, 49.48, 38.43, 24.28, 23.88. IR (KBr): 3399, 3367, 32223, 3161, 3074, 2967, 2839, 2410, 1904, 1722, 1656, 1615, 1598, 1499, 1458, 1407, 1351, 1314, 1242, 1234, 1169, 1109, 1098, 1086,1059, 1032, 1003, 982, 945, 922, 863, 829, 814, 774, 756, 731, 691, 663, 580, 532, 513, 495, 480, 468, 445, 426, 407, (cm$^{-1}$). Analysis calculated for C$_{23}$H$_{24}$Cl$_2$N$_4$O$_2$.C$_4$H$_4$O$_4$: C, 56.36; H, 4.90; N, 9.74; Found: C, 56.10; H, 5.06; N, 9.83

Example 11

8-CHLORO-3-[3-(3-p-TOLYL-3,8-DIAZA-BICYCLO[3.2.1]OCT-3-YL)-PROPYL]-1H-QUINAZOLINE-2,4-DIONE, MALEATE SALT

The title compound was made in a manner analogous to Example 10. White solid. Mp. 173–175° C., $^1$H NMR DMSO-d$_6$ δ: 11.06 (brd s, 1H), 9.31 (brd s, 1H), 7.92 (d, J=6.7 Hz, 1H), 7.79 (d, J=7.9 Hz, 1H), 7.00 (d, J=8.3 Hz, 2H), 6.77 (d, J=8.7 Hz, 2H), 5.99 (s, 2H), 4.08 (brd s, 2H), 3.98 (t, J=6.7 Hz, 2H), 3.63–3.50 (m, 2H), 3.14–2.94 (m, 4H), 2.16 (s, 3H), 2.14–2.00 (m, 4H), 1.99–1.56 (m, 2H);

Analysis calculated for $C_{24}H_{27}ClN_4O_2 \cdot C_4H_4O_4$: C, 60.59; H, 5.63; N, 10.09.

Example 12

3-[3-(3-P-TOLYL-3,8-DIAZA-BICYCLO[3.2.1] OCT-8-YL)-PROPYL]-1H-QUINAZOLINE-2,4-DIONE, MALEATE SALT

The title compound was made in a manner analogous to Example 10. White solid. Mp. 196–198° C., $^1$H NMR DMSO-d$_6$ δ:11.48, (s, 1H), 9.29 (brd s, 1H), 7.92 (d, J=7.9 Hz, 1H), 7.64 (t, J=7.0 Hz, 1H), 7.22–7.13 (m, 2H), 7.00 (d, J=8.3 Hz, 2H), 6.77 (d, J=8.3 Hz, 2H), 5.99 (s 2H), 4.09 (brd s, 2H), 3.96 (t, J=6.2 Hz, 2H), 3.64–3.49 (m, 2H), 3.13–2.93 (m, 4H), 2.16 (s, 3H), 2.13–1.98 (m, 4H), 1.96–1.89 (m, 2H). IR (KBr):3194, 3137, 3057, 2951, 2843, 2463, 1968, 1820, 1717, 1662, 1623, 1574, 1514, 1493, 1453, 1421, 1382, 1355, 1316, 1291, 1278, 1246, 1206, 1167, 1151, 1107, 1056, 1038, 981, 956, 942, 924, 873, 850, 814, 797, 787, 769, 755, 731, 712, 691, 681, 666, 644, 616, 583, 539, 528, 519, 496, 463, 438, 424, 404, (cm$^{-1}$). Analysis calculated or $C_{24}H_{28}N_4O_2 \cdot C_4H_4O_4 \cdot \frac{1}{3}H_2O$: C, 63.86; H, 6.25; N, 10.64. Found: C, 64.00; H, 6.30; N, 10.51.

Example 13

3-{3-[3-(4-CHLORO-PHENYL)-3,8-DIAZA-BICYCLO[3.2.1]OCT-8-YL]-PROPYL}-1H-QUINAZOLINE-2,4-DIONE, HYDROCHLORIDE SALT

The title compound was made in a manner analogous to Example 10. Off-white foam. Mp. 108–110° C. (decomposed); $^1$H NMR DMSO-d$_6$ δ: 11.05 (s, 1H), 10.33 (brd s, 1H), 7.92 (d, J=7.9 Hz, 1H), 7.79 (d, J=8.7 Hz, 1H), 7.25–7.16 (m, 3H), 6.89 (d, J=9.1 Hz, 3.97 (t, J=6.7 Hz, 2H), 3.63 (d, J=11.2 Hz, 2H), 3.25 (d, J=12.5 Hz, 2H), 3.12–3.02 (m, 2H0, 2.18–2.05 (m, 4H), 1.96–1.85 (m, 2H). IR (KBr): 3222, 3162, 3064, 2982, 2856, 2827, 2678, 2636, 2570, 2442, 2370, 1946, 1905, 1721, 1651, 1610, 1595, 1500, 1472, 1453, 1437, 1425, 1411, 1395, 1378, 1357, 1348, 1315, 1257, 1232, 1220, 1170, 1135, 1098, 1082, 1060, 1041, 1030, 988, 973, 946, 920, 881, 859, 844, 822, 804, 791, 753, 738, 704, 683, 672, 660, 584, 517, 495, 443, 424, 414, (cm$^{-1}$). Analysis calculated for $C_{23}H_{24}Cl_2N_4O_2 \cdot HCl \cdot 1\frac{1}{3}H_2O$: C, 53.14; H, 5.42; N, 10.77. Found: C, 53.29; H, 5.14; N, 10.65.

Example 14

3-{3-[3-(4-CHLORO-PHENYL)-3,8-DIAZA-BICYCLO[3.2.1]OCT-8-YL]-PROPYL}-6-METHYL-1H-QUINAZOLINE-2,4-DIONE HYDROCHLORIDE

The title compound was made in a manner analogous to Example 10. White solid. Mp. >300° C.; $^1$H NMR DMSO-d$_6$ δ: 11.43 (brd s, 1H), 10.30 (brd s, 1H), 7.72 (s, 1H), 7.47 (d, J=8.3 Hz, 1H), 7.22 (d, J=7.7 Hz, 2H), 7.09 (d, J=8.1 Hz, 1H), 6.89 (d, J=8.9 Hz, 2H), 4.12 (brd s, 2H), 3.96 (t, J=6.4 Hz, 2H), 3.62 (d, J=12.0 Hz, 2H), 3.23 (d, J=12.2 Hz, 2H), 3.10–3.00 (m, 2H), 2.31 (s, 3H), 2.17–2.01 (m, 4H), 1.96–1.86 (m, 2H). IR (KBr): 3249, 3145, 3961, 3009, 2984, 2960, 2920, 2856, 2675, 2628, 2566, 2436, 2356, 1939, 1881, 1719, 1641, 1596, 1571, 1499, 1453, 1409, 1399, 1371, 1351, 1323, 1276, 1266, 1254, 1247, 1230, 1216, 1185, 1167, 1158, 1128, 1100, 1062, 1039, 1024, 981, 920, 876, 860, 842, 824, 804, 784, 759, 732, 702, 673, 622, 584, 571, 544, 527, 512, 482, 456, 427, 407, (cm$^{-1}$). Analysis calculated for $C_{24}H_{27}ClN_4O_2 \cdot HCl \cdot 1/4\ H_2O$: C, 60.09; H, 5.99; N, 11.68. Found: C, 60.41; H, 6.15; N, 11.47.

Example 15

8-CHLORO-3-{3-[3-(2,4-DIMETHYL-PHENYL)-3,8-DIAZA-BICYCLO[3.2.1]OCT-8-YL]-PROPYL}-1H-QUINAZOLINE-2,4-DIONE, MALEATE SALT

The title compound was made in a manner analogous to Example 10. Tan solid. Mp. 217–219° C., $^1$H NMR DMSO-d$_6$ δ: 11.08 (s, 1H), 9.23 (brd s, 1H), 7.93 (dd, J=1.3, 6.6 Hz, 1H), 7.81 (dd, J=1.3, 6.6 Hz, 1H), 7.22 (t, J=7.9 Hz, 1H), 6.97 (brd s, 1H), 6.96–6.90 (m, 2H), 6.01 (s, 2H), 4.08–4.02 (m, 2H), 3.99 (t, J=7.1 Hz, 2H), 3.18–3.04 (m, 4H), 2.90 (d, J=11.6 Hz, 2H), 2.22 (s, 3H), 2.18 (s, 3H), 2.13 (s, 2H), 2.10–1.99 (m, 4H). IR (KBr): 3375, 3159, 3073, 2970, 2952, 2862, 2706, 2510, 1946, 1893, 1725, 1664, 1611, 1579, 1502, 1471, 1447, 1406, 1379, 1356, 1309, 1276, 1226, 1205, 1162, 1138, 1059, 1036, 978, 955, 916, 902, 869, 851, 824, 811, 791, 756, 741, 730, 704, 662, 645, 613, 575, 538, 523, 495, 473, 456, 448, 429, 406, (cm$^{-1}$). Analysis calculated for $C_{25}H_{29}ClN_4O_2 \cdot C_4H_4O_4 \cdot 3/4\ H_2O$: C, 59.79; H, 5.97; N, 9.62. Found: C, 60.09; H, 5.98; N, 9.17.

Example 16

8-CHLORO-3-{3-[3-(3,4-DICHLORO-PHENYL)-3,8-DIAZA-BICYCLO[3.2.1]OCT-8-YL]-PROPYL}-1H-QUINAZOLINE-2,4-DIONE, MALEATE SALT

The title compound was made in a manner analogous to Example 10. White solid. Mp. 205–207° C., $^1$H NMR DMSO-d$_6$ δ: 11.06 (s, 1H), 9.42 (brd s, 1H), 7.92 (d, J=7.9 Hz, 1H), 7.79 (d, J=7.9 Hz, 1H), 7.40 (d, J=9.1 Hz, 1H), 7.20 (t, J=7.9 Hz, 1H), 6.86 (d, J=8.7 Hz, 1H), 6.00 (s, 2H), 4.21–4.05 (m, 2H), 4.02–3.95 (m, 2H), 3.81–3.51 (m, 2H), 3.18–2.95 (m, 4H), 2.19–1.99 (m, 4H), 1.98–1.86 (m, 2H). IR (KBr): 3366, 3223, 3166, 3076, 3024, 2962, 2849, 2403, 1957, 1720, 1656, 1614, 1594, 1552, 1504, 1486, 1459, 1406, 1386, 1353, 1313, 1244, 1225, 1169, 1140, 1107, 1087, 1056, 1035, 1024, 981, 948, 911, 878, 862, 838, 804, 783, 755, 725, 704, 683, 666, 645, 585, 543, 494, 470, 443, 415, (cm$^{-1}$). Analysis calculated for $C_{23}H_{23}Cl_3N_4O_2 \cdot C_4H_4O_4 \cdot 1\frac{1}{2}H_2O$: C, 50.92; H, 4.74; N, 8.80. Found: C, 50.67; H, 4.27; N, 8.53.

Example 17

3-{3-[3-(3,4-DICHLORO-PHENYL)-3,8-DIAZA-BICYCLO[3.2.1]OCT-8-YL]-PROPYL}-1H-QUINAZOLINE-2,4-DIONE, MALEATE SALT

The title compound was made in a manner analogous to Example 10. Tan solid. Mp. 105–108° C. decompose, $^1$H NMR DMSO-d$_6$ δ: 11.49 (brd s, 1H), 9.41 (brd s, 1H), 7.92 (d, J=7.1 Hz, 1H), 7.65 (t, J=8.3 Hz, 1H), 7.40 (d, J=9.1Hz, 1H), 7.24–7.10 (m, 3H), 6.94–6.83 (m, 1H), 6.06 (s, 2H), 4.12 (brd s, 1H), 4.02–3.93 (m, 2H), 3.78–3.64 (m,2H), 3.15–3.00 (m, 2H), 2.20–1.99 (m, 4H), 1.95–1.87 (m, 2H). IR (KBr): 3048, 2972, 2886, 2562, 1717, 1658, 1622, 1594, 1487, 1455, 1407, 1351, 1263, 1172, 1014, 977, 950, 864, 832, 802, 758, 694, 682,656, 565,497, 464, 441, 428, 409, (cm$^{-1}$). Analysis calculated for $C_{23}H_{24}Cl_2N_4O_2 \cdot C_4H_4O_4 \cdot 1\frac{1}{2}H_2O$: C, 53.83; H, 5.18; N, 9.30. Found: C, 53.97; H, 4.83; N, 8.59.

Example 18

8-CHLORO-3-{3-[3-(4-FLUORO-PHENYL)-3,8-DIAZA-BICYCLO[3.2.1]OCT-8-YL]-PROPYL}-1H-QUINAZOLINE-2,4-DIONE, MALEATE SALT

The title compound was made in a manner analogous to Example 10. White solid. Mp. 173–175° C., $^1$H NMR DMSO-$d_6$ δ: 11.05 (brds, 1H), 9.34 (brd s, 1H), 7.92 (d, J=7.1 Hz, 1H), 7.79 (d, J=7.5 Hz, 1H), 7.20 (t, J=7.9 Hz, 1H), 7.03 (t, J=8.7 Hz, 2H), 6.94–6.83 (m, 2H), 5.98 (s, 2H), 4.19–4.04 (m, 2H), 3.98 (t, J=7.1 Hz, 2H), 3.67–3.49 (m, 2H), 3.16–2.93 (m, 4H), 2.22–1.99 (m, 6H); Analysis calculated for $C_{23}H_{24}ClFN_4O_2 \cdot C_4H_4O_4$: C, 56.40; H, 4.91; N, 9.74. Found: C, 57.24; H, 4.91; N, 9.49.

Example 19

3-{3-[3-(4-FLUORO-PHENYL)-3,8-DIAZA-BICYCLO[3.2.1]OCT-8-YL]-PROPYL}-1H-QUINAZOLINE-2,4-DIONE, MALEATE SALT

The title compound was made in a manner analogous to Example 10. White solid. Mp. 70–74° C., $^1$H NMR DMSO-$d_6$ δ: 11.50 (s, 1H), 9.34 (brds, 1H), 7.92 (d, J=7.5 Hz, 1H), 7.64 (t, J=7.5 Hz, 1H), 7.25–7.13 (m, 2H), 7.04 (t, J=8.7 Hz, 2H), 6.95–6.83 (m, 2H0, 6.00 (s, 2H), 4.11 (brd s, 2H), 4.01–3.90 (m, 2H), 3.64–3.53 (m, 2H), 3.40–3.23 (m, 2H), 3.15–2.96 (m, 4H), 2.17–2.00 (m, 4H); Analysis calculated for $C_{23}H_{25}FN_4O_2 \cdot C_4H_4O_4 \cdot 1 H_2O$: C, 59.77; H, 5.76; N, 10.32. Found: C 59.99; H, 5.58; N, 9.90.

Example 20

8-CHLORO-3-{3-[3-(4-TRIFLUOROMETHYL-PHENYL)-3,8-DIAZA-BICYCLO[3.2.1]OCT-8-YL]-PROPYL}-1H-QUINAZOLINE-2,4-DIONE, MALEATE SALT

The title compound was made in a manner analogous to Example 10. White solid. Mp. 205–207° C., $^1$H NMR DMSO-$d_6$ δ: 11.05 (brd s, 1H), 9.46 (brd s, 1H), 7.92 (d, J=7.9 Hz, 1H), 7.78 (d, J=7.9 Hz, 1H), 7.50 (d, J=8.3 Hz, 2H), 7.20 (t, J=7.9 Hz, 1H), 7.00 (d, J=7.9 Hz, 2H), 5.99 (s, 2H), 4.27–4.04 (m, 2H), 4.02–3.94 (m, 2H), 3.87–3.66 ( m, 2H), 3.31–3.24 (m, 2H), 3.22–2.97 (m, 2H), 2.21–1.98 (m, 4H0, 1.96–1.82 (m, 2H). IR (KBr): 3367, 3223, 3162, 3073, 2967, 2900, 2850, 2396, 1956, 1721, 1655, 1615, 1575, 1525, 1503, 1457, 1405, 1389, 1354, 1332, 1312, 1288, 1257, 1243, 1225, 1204, 1163, 1116, 1070, 1059, 1034, 976, 943, 925, 906, 879, 863, 830, 822, 780, 756, 727, 704, 689, 663, 652, 589, 572, 525, 512, 494, 465, 454, 443, 425, (cm$^{-1}$). Analysis calculated for Analysis calculated for $C_{24}H_{24}ClF_3N_4O_2 \cdot C_4H_4O_4$: C, 55.22; H, 4.63; N, 9.20. Found: C, 54.98; H, 4.89; N, 9.22.

Example 21

3-{3-[3-(4-TRIFLUOROMETHYL-PHENYL)-3,8-DIAZA-BICYCLO[3.2.1]OCT-8-YL]-PROPYL}-1H-QUINAZOLINE-2,4-DIONE, MALEATE SALT

The title compound was made in a manner analogous to Example 10. White foam. $^1$H NMR DMSO-$d_6$ δ: 11.48 (brd s, 1H), 9.48 (brd s, 1H), 7.92 (d, J=7.9 Hz, 1H), 7.64 (t, J=7.1 Hz, 1H), 7.51 (d, J=8.3 Hz, 2H), 7.17 (t, J=7.9 Hz, 2H), 7.01 (d, J=8.3 Hz, 2H), 4.20–4.02 (m,2H), 4.02–3.92 (m, 2H), 3.85–3.69 (m,2H), 3.21–2.97 (m, 4H), 2.21–1.98 (m, 4H), 1.93–1.80 (m,2H); Analysis calculated for $C_{24}H_{25}F_3N_4O_2 \cdot C_4H_4O_4$: C, 58.53; H, 5.09; N, 9.75.

Example 22

6,7-DIFLUORO-3-[3-(3-P-TOLYL-3,8-DIAZA-BICYCLO[3.2.1]OCT-8-YL)-PROPYL]-1H-QUINAZOLINE-2,4-DIONE, MALEATE SALT

The title compound was made in a manner analogous to Example 10. Off-white foam. Mp. 108–110° C. decomposed, $^1$H NMR DMSO-$d_6$ δ: 11.65 (brd s, 1H), 9.36 (brd s, 1H), 7.89 (t, J=9.6 Hz, 1H), 7.16–7.07 (m, 1H), 7.01 (d, J=7.9Hz, 2H), 6.77 (d, J=8.7 Hz, 2H), 6.05 (s, 2H), 4.10 (brd s, 2H), 3.94 (t, J=6.2 Hz, 2H), 3.66–3.53 (m, 2H), 3.14–2.94 (m, 4H), 2.16 (s, 3H), 2.14–1.87 (m, 6H); Analysis calculated for $C_{24}H_{26}F_2N_4O_2 \cdot C_4H_4O_4$: C, 60.43; H, 5.43; N, 10.07.

Example 23

6-FLUORO-3-[3-(3-P-TOLYL-3,8-DIAZA-BICYCLO[3.2.1]OCT-8-YL)-PROPYL]-1H-QUINAZOLINE-2,4-DIONE, MALEATE SALT

The title compound was made in a manner analogous to Example 10. Off-white foam. Mp. 108–110° C. decomposed, $^1$H NMR DMSO-$d_6$ δ: 11.56 (s, 1H), 9.34 (brd s, 1H), 7.63 (d, J=8.7 Hz, 1H), 7.58 (t, J=5.8 Hz, 1H), 7.25–7.17 (m, 1H), 7.01 (d, J=8.3 Hz, 2H), 6.78 (d, J=8.3 Hz, 2H), 6.03 (s, 2H), 4.11 (brd s, 2H), 3.96 (t, J=6.6 Hz, 2H), 3.59 (d, J=12.0 Hz, 2H), 3.13–2.95 (m, 4H), 2.17 (s, 3H), 2.15–1.90 (m, 6H); Analysis calculated for $C_{24}H_{27}FN_4O_2 \cdot C_4H_4O_4$: C, 62.44; H, 5.80; N, 10.40.

Examples 24–27

The following compounds were also made in a manner analogous to Example 10:

8-chloro-3-{3-[8-(4-chloro-phenyl)-3,8-diaza-bicyclo[3.2.1]oct-3-yl]-propyl}-1H-quinazoline-2,4-dione;

3-{3-[3-(4-chloro-phenyl)-8-aza-bicyclo[3.2.1]oct-8-yl]-propyl}-1H-quinazoline-2,4-dione;

3-[3-(3-phenyl-8-aza-bicyclo[3.2.1]oct-8-yl)-propyl]-1H-quinazoline-2,4-dione; and 3-[3-(3-p-tolyl-8-aza-bicyclo[3.2.1]oct-8-yl)-propyl]-1H-quinazoline-2,4-dione.

Example 28

2,2,2-TRIFLUORO-N-(4-HYDROXY-BUTYL)-ACETAMIDE 4-amino-1-butanol (15.0 g, 168.27 mmol) and methyl trifluoroacetate (82.96 mL, 824.55 mmol) were combined in methanol (250 mL) and heated at reflux for 2 hours. The reaction was concentrated to yield the title compound (26.6 g, 85.4%) as a clear oil which had the following properties: $^1$H NMR CDCl$_3$ δ: 7.08 (brd s, 1H), 3.71 (t, J=5.4 Hz, 2H), 3.40 (q, J=6.2 and 6.2 Hz, 2H), 1.75–1.61 (m, 4H).

Example 29

METHANESULFONIC ACID 4-(2,2,2-TRIFLUORO-ACETYLAMINO)-BUTYL ESTER 2,2,2-Trifluoro-N-(4-hydroxy-butyl)-acetamide (26.6 g, 143.66 mmol) and triethylamine 20.83 mL, 149.41 mmol) were combined in methylene chloride (290 mL) and cooled to 0° C. Methanesulfonic anhydride( 25.53 g, 146.54 mmol)

dissolved in methylene chloride (90 mL) was added to the reaction dropwise over 15 minutes and the resulting clear solution was stirred in the cold for 1 hour. Reaction after 1 h was incomplete thus added more methanesulfonic anhydride (5 g, 28.72 mmol) in one portion. The reaction was stirred an additional 1 h in the cold then diluted with water (500 mL) and extracted with diethyl ether (4×500 ml). The combined organic layers were dried with magnesium sulfate and concentrated to yield the title compound (27.6 g, 73%) as a white solid which had the following properties: $^1$H NMR CDCl$_3$ δ: 6.96 (brd s, 1H), 4.23 (t, J=6.2 Hz, 2H), 3.37 (q, J=6.7 and 6.7 Hz, 2H), 2.99 (s, 3H), 1.81–1.65 (m, 4H).

Example 30

N-{4-[3-(4-CHLORO-PHENYL)-3,8-DIAZA-BICYCLO[3.2.1]OCT-8-YL]-BUTYL}-2,2,2-TRIFLUORO-ACETAMIDE 3-(4-Chloro-phenyl)-3,8-diaza-bicyclo[3.2.1] octane hydrochloride salt (1.5 g, 5.79 mmol), triethylamine (1.77 mL, 12.73 mmol) and methanesulfonic acid 4-(2,2,2-trifluoro-acetylamino)-butyl ester (2.29 g, 8.68 mmol) were combined in tetrahydrofuran (25 mL). The resulting white heterogeneous reaction was heated at reflux for 24 hours. The mixture was cooled diluted with saturated sodium bicarbonate (200 mL) and extracted with ethyl acetate (3×100 mL). The combined organic layers were washed with brine (200 mL), dried with magnesium sulfate and concentrated to a light brown oil. Silica gel flash chromatography using 5% methanol/ chloroform as eluent yielded N-{4-[3-(4-Chloro-phenyl)-3,8-diaza-bicyclo[3.2.1]oct-8-yl]-butyl}-2,2,2-trifluoro-acetamide (0.88 9, 39%) as an off-white solid which had the following properties: Mp. 83–85° C., $^1$H NMR CDCl$_3$ δ: 7.77 (brd s, 1H), 7.16 (d, J=9.1 Hz, 2H), 6.68 (d, J=9.1 Hz, 2H), 3.44–3.35 (m, 4H), 3.29 (d, J=9.6 Hz, 2H), 3.02 (d, J=9.6 Hz, 2H), 2.51 (t, J=6.2 Hz, 2H), 2.10–1.90 (m, 2H), 1.83–1.76 (m, 2H), 1.73–1.57 (m, 6H).

Example 31

4-[3-(4-CHLORO-PHENYL)-3,8-DIAZA-BICYCLO[3.2.1]OCT-8-YL]-BUTYLAMINE

N-{4-[3-(4-Chloro-phenyl)-3,8-diaza-bicyclo[3.2.1]oct-8-yl]-butyl}-2,2,2-trifluoro-acetamide (0.88 g, 2.26 mmol) was dissolved in ethanol (18 mL) and 20% potassium hydroxide (3.26 mL). The clear solution was stirred for 3 hours, concentrated to dryness, diluted with methylene chloride (500 mL), added sodium sulfate and stirred for 3 hours. The mixture was filtered through Celite and concentrated to yield 4-[3-(4-Chloro-phenyl)-3,8-diaza-bicyclo[3.2.1]oct-8-yl]-butylamin (0.63 g, 94.9%) as a golden oil which had the following properties: $^1$H NMR CDCl$_3$ δ: 7.14 (d, J=9.1 Hz, 2H), 6.68 (d, J=9.1 Hz, 2H), 3.35 (brd s, 2H), 3.26 (d, J=13.7 Hz, 2H), 2.96 (d, J=9.1 Hz, 2H), 2.75–2.68 (m, 2H), 2.47–2.18 (m, 4H), 1.98–1.88 (m, 2H), 1.76–1.67 (m, 2H), 1.69–1.45 (m, 4H).

Example 32

8-CHLORO-3-{4-[3-(4-CHLORO-PHENYL)-3,8-DIAZA-BICYCLO[3.2.1]OCT-8-YL]-BUTYL}-1H-QUINAZOLINE-2,4-DIONE

2-Amino-3-chloro-benzoic acid methyl ester (0.126 g, .681 mmol) and triethylamine (0.22 mL, 1.57 mmol) were dissolved in methylene chloride (3 mL) and cooled to 0° C. Triphosgene (0.067 g, 0.227 mmol) in methylene chloride (1 mL) was added dropwise to the reaction and then stirred in the cold for 1 hour. Next 4-[3-(4-Chloro-phenyl)-3,8-diaza-bicyclo[3.2.1]oct-8-yl]-butylamine (0.20 g, 0.681 mmol) was added in one portion and the reaction was stirred at room temperature for 15 hours. Mix was evaporated to dryness, diluted with toluene (40 mL) and refluxed for 6 hours, cooled, diluted with saturated sodium bicarbonate (200 mL) and extracted with ethyl acetate (3×100 mL). The combined organic layers were washed with brine (200 mL), dried with magnesium sulfate and concentrated to a light brown solid. Silica gel flash chromatography using 3.5% methanol/chloroform as eluent yielded 8-Chloro-3-{4-[3-(4-chloro-phenyl)-3,8-diaza-bicyclo[3.2.1]oct-8-yl]-butyl}-1H-quinazoline-2,4-dione (0.198 g, 61%) as a white solid. Maleate salt was formed by dissolving the solid in warm chloroform (30 ml) and maleic acid (0.058 g, 1.2 eq) in warm ethyl acetate (20 ml) was added. Cooling yielded the maleate salt (0.196 g) as a white solid which had the following properties: Mp. 235–238° C., $^1$H NMR DMSO-d$_6$ δ: 11.02 (brd s, 1H), 9.85 (brd s, 1H), 7.91 (d, J=7.1 Hz, 1H), 7.79 (d, J=6.6 Hz, 1H), 7.26–7.18 (m, 3H), 6.90 (d, J=9.1 Hz, 2H), 6.00 (s, 2H), 4.17 (brd s, 2H), 3.98–3.87 (m, 2H), 3.66 (d, J=14.1 Hz, 2H), 3.11–2.93 ( m,4H), 2.19–2.06 (m, 2H), 1.97–1.85 (m, 2H), 1.77–1.6 (m, 4H). IR (KBr): 3355, 3216, 3190, 3161, 3071, 2960, 2849, 2706, 2397, 1717, 1655, 1610, 1500, 1473, 1456, 1435, 1420, 1404, 1365, 1332, 1311, 1269, 1254, 1221, 1185, 1163, 1134, 1101, 1068, 1041, 989, 973, 954, 925, 915, 882, 851, 821, 814, 790, 761, 747, 729, 701, 671, 650, 580, 545, 515, 496, 484, 437, 411, 404, (cm$^{-1}$). Analysis calculated for $C_{24}H_{26}Cl_2N_4O_2 \cdot C_4H_4O_4 \cdot 1½ H_2O$: C, 54.55; H, 5.39; N, 9.08. Found: C, 54.81; H, 5.06; N, 8.91.

Example 33

3-{4-[3-(4-CHLORO-PHENYL)-3,8-DIAZA-BICYCLO[3.2.1]OCT-8-YL]-BUTYL}-6-METHYL-1H-QUINAZOLINE-2,4-DIONE, MALEATE SALT

White solid. Mp. 222–224° C., $^1$H NMR DMSO-d$_6$ δ: 11.37 (s, 1H), 9.35 (brd s, 1H), 7.70 (brd s, 1H), 7.46 (d, J=8.3 Hz, 1H), 7.24 (d, J=9.1 Hz, 2H), 7.06 (d, J=7.9 Hz, 1H), 6.90 (d, J=9.1 Hz, 2H), 6.01 (s, 2H), 4.10 (brd s, 2H), 3.97–3.87 (m, 2H), 3.70–3.58 (m, 2H), 3.11–2.94 (m, 4H), 2.30 (s, 3H), 2.20–2.08 (m, 2H), 1.97–1.87 (m, 2H), 1.76–1.58 (m, 4H). IR (KBr): 3194, 3042, 2997, 2958, 2831, 2756, 2554, 1930, 1855, 1714, 1656, 1627, 1583, 1511, 1497, 1452, 1388, 1362, 1332, 1279, 1253, 1237, 1193, 1169, 1123, 1102, 1080, 1068, 1018, 986, 970, 927, 916, 883, 873, 849, 827, 809, 780, 762, 746, 733, 699, 677, 655, 621, 580, 558, 548, 537, 523, 513, 485, 460, 431, 417, (cm$^{-1}$). Analysis calculated for $C_{24}H_{26}Cl_2N_4O_2 \cdot C_4H_4O_4 \cdot ⅓ H_2O$: C, 60.57; H, 5.90; N, 9.74. Found: C, 60.58; H, 5.91; N, 9.58.

Example 34

3-{4-[3-(4-CHLORO-PHENYL)-3,8-DIAZA-BICYCLO[3.2.1]OCT-8-YL]-BUTYL}-1H-QUINAZOLINE-2,4-DIONE, MALEATE SALT

White solid. Mp. 187–189° C., $^1$H NMR DMSO-d$_6$ δ: 11.46 (s, 1H), 9.36 (brd s, 1H), 7.91 (d, J=7.9 Hz, 1H), 7.64 (t, J=7.5 Hz, 1H), 7.27–7.13 (m, 4H), 6.90 (d, J=8.7 Hz, 2H), 6.00 (s, 2H), 4.16–4.06 (m, 2H), 3.97–3.91 (m, 2H), 3.66 (d, J=12.0 Hz, 2H), 3.10–2.97 (m, 4H), 2.20–2.10 (m, 2H), 2.00–1.88 (m, 2H), 1.76–1.60 (m, 4H).

Example 35

1-(4-CHLORO-PHENYL)-PYRROLIDINE-2,5-DICARBOXYLIC ACID DIETHYL ESTER

Diethyl meso 2,5-dibromo adipate (5.0 g, 13.89 mmol), 4-chloro-aniline (6.2 g, 48.60 mmol), potassium iodide (0.032 g, 0.193 mmol) were combined and heated at 80° C. for 3 h then 90° C. for ½ hour. Mix was cooled, diluted with 6N hydrochloric acid (400 mL) and extracted with ethyl acetate (3×400 mL). The combined organic layers were washed with water (5×200 mL), brine (200 mL), dried with magnesium sulfate and concentrated to yield a mixture of cis and trans 1-(4-Chloro-phenyl)-pyrrolidine-2,5-dicarboxylic acid diethyl ester (4.53 g, 100%) as a brown oil. Oil was used without further purification.

Example 36

[1-(4-CHLORO-PHENYL)-5-HYDROXYMETHYL-PYRROLIDIN-2-YL]-METHANOL

Lithium aluminum hydride (1.0 M in tetrahydrofuran, 20.7 mL) was added to tetrahydrofuran (68 mL) at 0° C. 1-(4-Chloro-phenyl)-pyrrolidine-2,5-dicarboxylic acid diethyl ester (4.50 g, 13.81 mmol) in tetrahydrofuran (17 mL) was added rapidly dropwise and the mixture was stirred at room temperature for 4 hours. Mix was quenched by careful addition of water (2.5 mL) followed by 10% sodium hydroxide (1.7 mL) and stirred for 15 h then filtered through Celite and the cake was washed with ethyl acetate (2×100 mL). The filtrate was dried with magnesium sulfate and concentrated to yield a mixture of cis and trans [1-(4-Chloro-phenyl)-5-hydroxymethyl-pyrrolidin-2-yl]-methanol (3.34 g, 100%) as a golden oil. Oil was used without further purification.

Example 37

2,5-BIS-CHLOROMETHYL-1-(4-CHLORO-PHENYL)-PYRROLIDINE

[1-(4-Chloro-phenyl)-5-hydroxymethyl-pyrrolidin-2-yl]-methanol (3.28 g, 13.57 mmol) in dioxane (30 mL) was cooled to 0° C. and thionyl chloride (2.99 mL, 40.98 mmol) was added dropwise which caused the reaction to gum out of solution. Mixture was stirred at room temperature for 2 h which yielded a brown solution. The reaction was evaporated to dryness which yielded cis and trans 2,5-Bis-chloromethyl-1-(4-chloro-phenyl)-pyrrolidine as a brown oil (3.73 g, 100%). Oil was used without further purification.

Example 38

3-BENZYL-8-(4-CHLORO-PHENYL)-3,8-DIAZA-BICYCLO[3.2.1]OCTANE 2,5-Bis-chloromethyl-1-(4-chloro-phenyl)-pyrrolidine (3.73 g, 13.57 mmol), potassium carbonate (3.75 g, 27.14 mmol), and benzyl amine (4.45 mL, 40.71 mmol) in diglyme (25 mL) was heated at reflux for 15 hours. The reaction mixture was cooled to room temperature, diluted with diethyl ether (600 mL) and washed with water (6×300 mL). The combined organic layers were dried with magnesium sulfate and concentrated to a brown oil. Silica gel flash chromatography using 50% chloroform/hexanes as eluent yielded 3-Benzyl-8-(4-chloro-phenyl)-3,8-diaza-bicyclo [3.2.1]octane (1.0 g, 23.5%) as a golden solid which had the following properties: Mp. 115–117° C.; $^1$H NMR CDCl$_3$ δ: 7.29 (s, 5H), 7.14 (d, J=8.1 Hz, 2H), 6.67 (d, J=8.3 Hz, 2H), 4.08 (brd s, 2H), 3.38 (s, 2H), 2.54–2.42 (m, 4H), 2.08–2.00 (m,2H), 1.95–1.86 (m,2H).

Example 39

8-CHLORO-3-{3-[8-(4-CHLORO-PHENYL)-3,8-DIAZA-BICYCLO[3.2.1]OCT-3-YL]-PROPYL}-1H-QUINAZOLINE-2,4-DIONE, HYDROCHORIDE SALT

The title compound was prepared using 8-(4-chloro-phenyl)-3,8-diaza-bicyclo[3.2.1]octane as starting material. White solid. Mp. 167–169° C., $^1$H NMR DMSO-d$_6$ δ: 10.99 (brd s, 1H), 7.88 (d, J=7.9 Hz, 1H), 7.77 (d, J=7.9 Hz, 1H), 7.25–7.15 (m, 3H), 6.87 (d, J=8.3 Hz, 2H), 4.39 (brd s, 2H), 3.91–3.83 (m, 2H), 3.23 (d, J=11.6 Hz, 2H), 3.05–2.88 (m, 4H), 2.16 (d, J=7.5 Hz, 2H), 2.07–1.85 (m, 4H).

Example 40

8-CHLORO-3-[3-(8-P-TOLYL-3,8-DIAZA-BICYCLO[3.2.1]OCT-3-YL)-PROPYL]-1H-QUINAZOLINE-2,4-DIONE, MALEATE SALT

White solid. Mp. 205–207° C., $^1$H NMR DMSO-d$_6$ δ: 11.01 (s, 1H), 8.97 (brd s, 1H), 7.89 (d, J=7.9 Hz, 2H), 7.78 (d, J=7.9 Hz, 1H), 7.19 (t, J=7.9 Hz, 1H), 6.99 (d, J=7.9 Hz, 2H), 6.03 (s, 2H), 4.31 (brd s, 2H), 3.89 (t, J=6.2 Hz, 2H), 3.41–3.10 (m, 2H), 3.06–2.71 (m, 4H), 2.15 (s, 3H), 2.00–1.82 (m, 6H).

Example 41

8-CHLORO-3-{3-[5-(4-CHLORO-PHENYL)-2,5-DIAZA-BICYCLO[2.2.1]HEPT-2-YL]-PROPYL}-1H-QUINAZOLINE-2,4-DIONE, MALEATE SALT

Off-white solid. Mp. 205–207° C., $^1$H NMR DMSO-d$_6$ δ: 11.04 (s, 1H), 8.99 (brd s,1H), 7.90 (dd, J=1.25 & 7.9 Hz, 1H), 7.79 (dd, J=1.7 & 6.2 Hz, 7.24–7.16 (m, 3H), 6.64 (d, J=9.1 Hz, 2H), 5.98 (s, 2H), 4.56 (brd s, 1H), 4.35 (brd s, 1H), 3.94 (t, J=6.2 Hz, 2H), 3.62–3.06 (m,6H), 2.31–2.21 (m, 1H), 2.12–2.03 (m, 1H), 1.97–1.84 (m, 2H); Analysis calculated for C$_{22}$H$_{22}$Cl$_2$N$_4$O$_2$.C$_4$H$_4$O$_4$: C, 55.62; H, 4.67; N, 9.98.

Example 42

8-CHLORO-3-{3-[5-(3-FLUORO-PHENYL)-2,5-DIAZA-BICYCLO[2.2.1]HEPT-2-YL]-PROPYL}-1H-QUINAZOLINE-2,4-DIONE, MALEATE SALT

Off-white solid. Mp. 168–170° C., $^1$H NMR DMSO-d$_6$ 6: 11.05 (brd s, 1H), 8.98 (brd s, 1H), 7.90 (dd, J=1.2–6.4 Hz, 1H), 7.79 (dd, J=1.2 & 6.4 Hz, 1H), 7.23–7.13 (m, 2H), 6.55–6.39 (m, 3H), 5.99 (s, 1H), 4.59 (brd s, 1H), 4.36 (brd s, 1H), 4.36 (brd s, 1H), 3.94 (t, J=6.2 Hz, 2H), 3.61–3.43 (m, 2H), 3.36 (s, 2H), 3.21–3.10 (m, 2H), 2.27 (d, J=13.3 Hz, 1H), 2.08 (d, J=10.0 Hz, 1H), 1.92 (brd s, 2H); Analysis calculated for C$_{22}$H$_{22}$ClFN$_4$O$_2$.C$_4$H$_4$O$_4$: C, 57.30; H, 4.81; N, 10.28.

Example 43

8-BENZYL-3-(4-FLUORO-PHENYL)-3,8-DIAZA-BICYCLO[3.2.1]OCTANE AND 2-BENZYL-5-(4-FLUORO-PHENYL)-2,5-DIAZA-BICYCLO[2.2.2]OCTANE

1-Benzyl-2,5-bis-chloromethyl-pyrrolidine (10 g, 38.73 mmol), 4-fluoroaniline (4.30 g, 38.73 mmol) and potassium carbonate (5.35 g, 38.73 mmol) was combined in diglyme (26 ml) and heated at reflux for 15 hours. The mixture was cooled to room temperature, diluted with $H_2O$ (200 ml) and extracted with ethyl acetate (5×600 ml). The combined organic layers were washed with $H_2O$ (3×100 ml at pH 12, adjusted with potassium hydroxide), dried over magnesium sulfate and concentrated to a light brown oil. Silica gel flash chromatography using 5% ethyl acetate/hexanes as eluent yielded the less polar component to be 8-Benzyl-3-(4-fluoro-phenyl)-3,8-diaza-bicyclo[3.2.1]octane (2.9 g, 25.2%) as an off white solid which had the following properties. Mp. 100–102° C.; $^1$H NMR $CDCl_3$ δ: 7.40 (d, J=7.5 Hz, 2H), 7.32 (t, J=8.3 Hz, 2H), 7.27–7.22 (m, 1H), 6.92 (t, J=8.3 Hz, 2H), 6.74–6.68 (m, 2H), 3.59 (s, 2H), 3.33–3.26 (m, 2H), 3.25–3.22 (m,2H), 2.98 (dd, J=1.7 &8.7 Hz, 2H), 2.08–2.00 (m, 2H), 1.84–1.77 (m,2H). Analysis calculated for $C_{19}H_{21}FN_2$: C, 77.00; H, 7.14; N, 9.45. Found: C, 77.26; H, 7.40; N, 9.44

More polar component from chromatography yielded 2-Benzyl-5-(4-fluoro-phenyl)-2,5-diaza-bicyclo[2.2.2] octane as a tan solid which had the following properties: Mp. 74–76° C.; $^1$H NMR $CDCl_3$ δ: 7.38–7.27 (m, 4H), 6.92 (t, J=8.3 Hz, 2H), 6.57–6.51 (m, 2H), 3.81–3.68 (m, 4H), 3.16 (dd, J=2.0 & 7.9 Hz, 1H), 3.00 (d, J=2.5 Hz, 1H), 2.97 (d, J=2.1 Hz, 1H), 2.95 (t, J=2.5 Hz, 1H), 2.90–2.85 (m, 1H), 2.14–2.05 (m, 1H), 2.00–1.90 (m, 1H), 1.87–1.78 (M, 1H), 1.65–1.56 (m, 1H). Analysis calculated for $C_{19}H_{21}FN_2$: C, 77.00; H, 7.14; N, 9.45. Found: C, 77.22; H, 7.45; N, 9.58.

Example 44

3-(4-FLUORO-PHENYL)-3,8-DIAZA-BICYCLO [3.2.1]OCTANE

8-Benzyl-3-(4-fluoro-phenyl)-3,8-diaza-bicyclo[3.2.1] octane (2.7 g, 9.11 mmol) was dissolved in 1N hydrochloric acid/methanol (150 mL) and under nitrogen 10% palladium on carbon (1.4 g) was added. The reaction was hydrogenated at 1 atmosphere for 2 hours. The reaction was filtered through Celite and concentrated to yield 3-(4-Fluoro-phenyl)-3,8-diaza-bicyclo[3.2.1]octane, hydrochoride salt (2.2 g, 100%) as a white solid which had the following properties: Mp. 129–131° C.; $^1$H NMR $CDCl_3$ δ: 9.69 (brd s, 1H), 7.07–6.95 (m, 2H), 6.90–6.80 (m, 2H), 4.05 (brd s, 2H), 3.49 (d, J=10.4 Hz, 2H), 3.08 (d, J=11.2 Hz, 2H), 2.00–1.84 (m, 2H).

Example 45

2-(4-FLUORO-PHENYL)-2,5-DIAZA-BICYCLO [2.2.2]OCTANE

2-Benzyl-5-(4-fluoro-phenyl)-2,5-diaza-bicyclo[2.2.2] octane (1.1 g, 3.71 mmol) was dissolved in 1N hydrochloric acid/methanol (60 mL) and under nitrogen 10% palladium on carbon (0.50 g) was added. The reaction was hydrogenated at 1 atmosphere for 2 hours. The reaction was filtered through Celite and concentrated to yield 2-(4-Fluoro-phenyl)-2,5-diaza-bicyclo[2.2.2]octane, hydrochoride salt (0.90 g, 100%) as an off white solid which had the following properties. Mp. 154–156° C.; $^1$H NMR $CDCl_3$ δ: 9.74 (brd s, 1H), 9.67 (brd s, 1H), 7.00 (t, J=9.1 Hz, 2H), 6.68–6.61 (m, 2H), 4.07 (s, 1H), 3.70 (brd s, 1H), 3.63 (d, J=11.2 Hz, 1H), 3.29 (d, J=10.8 Hz, 1H), 3.23 (brd s, 2H), 2.19–2.04 (m, 1H), 1.95–1.83 (m, 1H), 1.81–1.64 (m, 2H).

Example 46

8-CHLORO-3-{3-[5-(4-FLUORO-PHENYL)-2,5-DIAZA-BICYCLO[2.2.2]OCT-2-YL]-PROPYL}-1H-QUINAZOLINE-2,4-DIONE

8-Chloro-3,4-dihydro-2H-1-oxa-4a,9-diaza-anthracen-10-one (0.35, 1.49 mmol), 2-(4-Fluoro-phenyl)-2,5-diaza-bicyclo[2.2.2]octane (HCl salt) (0.30g, 1.24 mmol), triethylamine (0.21 ml, 1.49 mmol), p-toluene sulfonic acid (0.036 g, 0.187 mmol) were combined in dimethyl acetamide (2 ml) and heated at 120° C. for 15 hours. The reaction was cooled to room temperature, diluted with $H_2O$ (200 mL) and extracted with ethyl acetate (3×100 mL). The pooled organic layers were washed with water (3×200 mL),dried over magnesium sulfate, and concentrated to a brown semi-solid. Silica gel flash chromatography using 5% methanol/ chloroform as the eluent yielded 8-Chloro-3-{3-[5-(4-fluoro-phenyl)-2,5-diaza-bicyclo[2.2.2]oct-2-yl]-propyl}-1H-quinazoline-2,4-dione (0.18 g, 32.7%) as an light brown solid Maleate salt was formed by dissolving the solid in hot ethyl acetate (5 ml) and maleic acid (0.57 g, 1.2 eq) in ethyl acetate (4 ml) was added. Upon cooling the white solid was filtered to yield the maleate salt (0.12 g) which had the following properties: Mp. 186–188° C.; $^1$H NMR DMSO-$d_6$ δ: 11.04 (brds, 1H), 9.40 (brd s, 1H), 7.91 (d, J=7.9 Hz, 1H), 7.79 (d, J=7.9 Hz, 1H), 7.20 (t, J=7.9 Hz, 1H), 6.68 (brds, 2H), 6.02 (s, 2H), 4.11 (brds, 1H), 4.02–3.92 (m, 2H), 3.80–3.52 (m, 3H), 3.44–3.17 (m, 4H), 2.18–1.65 9m, 6H). IR(KBr): Analysis calculated for $C_{23}H_{24}ClFN_4O_2$* $C_4H_4O_4$: C, 56.40; H, 4.91; N, 9.74;

Example 47

8-CHLORO-3-{3-[5-(2,4-DIMETHYL-PHENYL)-2,5-DIAZA-BICYCLO[2.2.2]OCT-2-YL]-PROPYL}-1H-QUINAZOLINE-2,4-DIONE, MALEATE SALT

White glass, Mp. 149–151° C.; $^1$H NMR DMSO-$d_6$ δ: 11.05 (brd s, 1H), 9.57–9.12 (brds, 1H), 7.92 (d, J=7.5 Hz, 1H), 7.80 (d, J=7.9 Hz, 1H), 7.044.82 (m, 3H), 5.98 (s, 2H), 3.98 (t, J=6.7 Hz, 2H), 3.83–3.00 (m, 6H), 2.16 (s, 3H), 2.14 (s, 3H), 2.07–1.86 (m, 6H). IR (KBr): 3360, 3160, 3075, 2963, 2461, 1718, 1653, 1616, 1574, 1504, 1474, 1411, 1379, 1356, 1315, 1270, 1242, 1194, 1137, 1081, 977, 944, 904, 870, 813, 757, 725, 665, 648, 582, 563, 540, 493, 472, 459, 438, 421, 413, 405, (cm$^{-1}$).

Example 48

8-CHLORO-3-{3-[5-(3,4-DICHLORO-PHENYL)-2,5-DIAZA-BICYCLO[2.2.2]OCT-2-YL]-PROPYL}-1H-QUINAZOLINE-2,4-DIONE, MALEATE SALT

Off-white solid. Mp. 68–73° C., decomposed, $^1$H NMR DMSO-$d_6$ δ: 11.04 (s, 1H), 9.29 (brd s, 1H), 7.91 (d, J=7.9 Hz, 1H), 7.79 (d, J=7.9 Hz, 1H), 7.86 (d, J=9.1 Hz, 1H), 7.20 (t, J=7.9 Hz, 1H), 6.98–6.82 (m, 1H), 6.72–6.63 (m, 1H), 6.0 (s, 2H), 4.24–4.18 (m, 1H), 4.00–3.90 (m, 2H), 3.83–3.51 (m, 3H), 3.46–3.12 (m, 4H), 2.17–1.65 (m, 6H).

Example 49

3-{3-[5-(4-FLUORO-PHENYL)-2,5-DIAZA-BICYCLO[2.2.2]OCT-2-YL]-PROPYL}-1H-QUINAZOLINE-2,4-DIONE, MALEATE SALT

Tan solid. Mp. 95–98° C., decomposed, $^1$H NMR DMSO-$d_6$ δ: 11.46 (brd s, 1H), 9.31 (brd s, 1H), 7.91 (d, J=7.5 Hz, 1H), 7.64 (t, J=7.5 Hz, 1H), 7.25–7.13 (m, 2H), 7.02 (t, J=8.7 Hx, 2H), 6.69 (brd s, 2H), 6.06 (s, 2H), 4.11 (brds, 1H), 3.96 (brd s, 2H), 3.83–3.53 (m, 3H), 3.47–3.09 (m, 4H), 2.21–1.64 (m, 6H).

Example 50

RACEMIC 3-(4-CHLORO-PHENYL)-8-METHYL-8-AZA-BICYCLO[3.2.1]OCTAN-3-OL 2.5 M n-butyl lithium (17.96 mL, 40.90 mmol) was added to -70 ° C diethyl ether (35 mL) and 4-bromochlorobenzene (9.03 g, 47.15 mmol) in diethyl ether (20mL) was added dropwise over 20 minutes. The mixture was stirred in the cold for 20 minutes then 8-Methyl-8-aza-bicyclo[3.2.1] octan-3-one (5 g, 35.92 mmol) in diethyl ether (12 mL) was added dropwise over 5 minutes. Cooling bath was removed and when internal temperature of −20° C. was reached the solution was quenched with 1N hydrochloric acid (200 mL). The aqueous layer was raised to pH=10 with ammonium hydroxide and extracted with diethyl ether (three times, 200 mL each). The combined organic layers were washed with brine (100 mL), dried with magnesium sulfate and concentrated to yield racemic3-(4-Chloro-phenyl)-8-methyl-8-aza-bicyclo[3.2.1]octan-3-ol (6.87 g, contains 9% 8-Methyl-8-aza-bicyclo[3.2.1]octan-3-one) as a white solid. Solid was used without further purification.

Example 51

RACEMIC 3-(4-CHLORO-PHENYL)-8-METHYL-8-AZA-BICYCLO[3.2.1]OCT-2-ENE

Racemic 3-(4-Chloro-phenyl)-8-methyl-8-aza-bicyclo[3.2.1]octan-3-ol (6.37 g, 25.30 mmol) was dissolved in trifluoroacetic acid (30.8 mL) and heated at reflux for 1 hour. The reaction was concentrated diluted with water (200 mL), adjusted to pH 10 with ammonium hydroxide, and extracted with diethyl ether (2×200 mL). The combined organic layers were washed with brine (100 mL), dried with magnesium sulfate and concentrated to yield racemic 3-(4-Chloro-phenyl)-8-methyl-8-aza-bicyclo[3.2.1]oct-2-ene as a white solid which had the following properties: Mp. 82–84° C., $^1$H NMR CDCl$_3$ δ: 7.27 (q, J=7.7 & 8.5 Hz, 4H), 6.24 (d, J=5.6 Hz, 1H), 3.45–3.36 (m, 2H), 2.82 (dd, J=4.2 & 12.7 Hz, 1H), 2.37 (s, 3H), 2.23–2.14 (m, 1H), 2.13–2.03 (m, 1H), 1.98 (d, J=17.2 Hz, 1H), 1.91–1.83 (m, 1H), 1.62–1.53 (m, 1H). IR (KBr): 3096, 3079, 3049, 3023, 2945, 2904, 2847, 2798, 2764, 2708, 2596, 2315, 2212, 1942, 1910, 1747, 1667, 1587, 1562, 1532, 1496, 1470, 1443, 1429, 1419, 1406, 1356, 1318, 1302, 1276, 1259, 1244, 1213, 1198, 1164, 1146, 1130, 1109, 1093, 1074, 1059, 1009, 992, 969, 942, 918, 873, 852, 834, 813, 799, 777, 746, 728, 706, 675, 632, 575, 546, 532, 469, 443, 414, (cm$^{-1}$). Analysis calculated for C$_{14}$H$_{16}$ClN: C, 71.94; H, 6.90; N, 5.99. Found: C, 71.88, H, 7.20, N, 6.00.

Example 52

RACEMIC 3-(4-CHLORO-PHENYL)-8-AZA-BICYCLO[3.2.1]OCT-2-ENE-8-CARBOXYLIC ACID, 2,2,2-TRICHLORO-ETHYL ESTER

Racemic 3-(4-Chloro-phenyl)-8-methyl-8-aza-bicyclo[3.2.1]oct-2-ene (4.98 g, 21.31 mmol) in 1,1,1-trichloroethane (60 mL) was heated at reflux and 2,2,2-trichloroethyl chloroformate (3.23 mL, 23.44 mmol) was added dropwise over 10 minutes. The reaction was refluxed for 3 hours, cooled and concentrated to a clear oil. Silica gel flash chromatography using 5% methanol/chloroform as the eluent yielded racemic 3-(4-Chloro-phenyl)-8-aza-bicyclo[3.2.1]oct-2-ene-8-carboxylic acid 2,2,2-trichloro-ethyl ester (7.77 g, 92.2%) as a clear oil which had the following properties: $^1$H NMR CDCl$_3$ δ: 7.25 (s, 4H), 6.41 (m, 1H), 4.85 (m, 1H), 4.73 (s, 1H), 4.68–4.76 (m, 2H), 3.12 (d, J=17 Hz, 1H), 2.25 (m, 2H), 2.03 (m, 2H), 1.75 (m, 1H).

Example 53

RACEMIC 3-(4-CHLORO-PHENYL)-8-AZA-BICYCLO[3.2.1]OCT-2-ENE

Racemic 3-(4-Chloro-phenyl)-8-aza-bicyclo[3.2.1]oct-2-ene-8-carboxylic acid #2,2,2-trichloro-ethyl ester (7.5 g, 18.98 mmol) in acetic acid (75 mL) and water (10 mL) was heated at 45° C. Zinc (16.63 g, 257.39 mmol) was added portionwise to the reaction over 1 hour. Mix was filtered through Celite and the filtrate was concentrated to a clear oil. The oil was dissolved in water (100 mL) adjusted to PH=12 with 1N sodium hydroxide and extracted with ethyl acetate (2×200 mL). The combined organic layer was washed with brine (100 mL), dried with magnesium sulfate and concentrated to yield racemic 3-(4-Chloro-phenyl)-8-aza-bicyclo [3.2.1]oct-2-ene (3.4 g, 81.5%) as a white solid with had the following properties: Mp 91–93° C.; $^1$H NMR CDCl$_3$ δ: 7.30–7.21 (m, 4H), 6.41 (d, J=5.6 Hz, 1H), 3.85 (t, J=5.6 Hz, 1H), 3.80 (t, J=5.6 Hzm 1H), 2.80 (d, J=17.2 Hz, 1H), 2.17 (d, J=17.2 Hz, 1H), 2.11–1.69 (m, 3H), 1.66–1.57 (m, 1H). IR (KBr): 3965, 3887, 3721, 3664, 3477, 3304, 3237, 3081, 3048, 3020, 2966, 2928, 2882, 2835, 2710, 2675, 2595, 2495, 2425, 2396, 2362, 2314, 2104, 1967, 1935, 1913, 1894, 1847, 1791, 1707, 1630, 1589, 1563, 1494, 1466, 1446, 1428, 1403, 1380, 1360, 1341, 1307, 1279, 1249, 1239, 1221, 1190, 1151, 1092, 1068, 1030, 1008, 973, 948, 935, 916, 876, 850, 811, 755, 738, 726, 706, 672, 665, 631, 610, 554, 544, 524, 519, 469, 445, 433, 421, (cm$^{-1}$). Analysis calculated for C$_{13}$H$_{14}$ClN.⅓ H$_2$O: C, 69.18; H, 6.55; N, 6.21; Found: C, 69.42; H, 6.36; N, 6.15.

Example 54

RACEMIC N-{3-[3-(4-CHLORO-PHENYL)-8-AZA-BICYCLO[3.2.1]-OCT-2-EN-8-YL]-PROPYL}-2,2,2-TRIFLUORO-ACETAMIDE

Racemic 3-(4-Chloro-phenyl)-8-aza-bicyclo[3.2.1]oct-2-ene (1.0 g, 4.55 mmol), triethylamine (0.70 mL, 5.01 mmol), and methanesulfonic acid 3-(2,2,2-trifluoro-acetylamino)-propyl ester (1.13 g, 4.55 mmol) in ethanol (20 mL) were refluxed for 15 hours. The mix was concentrated, diluted with saturated sodium bicarbonate (200 mL) and extracted with ethyl acetate (3×150 mL). Combined organic layers were washed with brine (200 mL), dried with magnesium sulfate and concentrated to a light brown oil. Silica gel flash chromatography using 5% methanol/chloroform as the eluent yielded racemic N-{3-[3-(4-Chloro-phenyl)-8-aza-bicyclo[3.2.1]oct-2-en-8-yl]-propyl}-2,2,2-trifluoro-acetamide (0.79 g, 46.5%) as a light brown oil which had the following properties: $^1$H NMR CDCl$_3$ δ: 10.00 (brd s, 1H), 7.27 (s, 4H), 6.23 (d, J=5.4 Hz, 1H), 3.69–3.43 (m, 4H), 2.82–2.71 (m, 3H), 2.19–1.88 (m, 4H), 1.77–1.57 (m, 3H). IR (CHCl$_3$): 3157, 2949, 2880, 1714, 1544, 1494, 1466, 1446, 1403, 1377, 1346, 1315, 1245, 1162, 1094, 1012, 973, 937, 817, (cm$^{-1}$). Analysis calculated for C$_{18}$H$_{20}$ClF$_3$N$_2$O.3/4 H$_2$O: C, 55.96; H, 5.61; N, 7.25; Found: C, 55.80; H, 5.09; N, 7.33.

Example 55

3-[3-(4-CHLORO-PHENYL)-8-AZA-BICYCLO[3.2.1]OCT-2-EN-8-YL]-PROPYLAMINE

Racemic N-{3-[3-(4-Chloro-phenyl)-8-aza-bicyclo[3.2.1]oct-2-en-8-yl]-propyl}-2,2,2-trifluoroacetamide (0.73 g, 1.96 mmol) and 20% potassium hydroxide (2.8 mL) were combined in ethanol (12 mL) and stirred at room temperature for 24 hours. Reaction was concentrated, dissolved in methylene chloride (200 mL), added sodium sulfate and stirred for 15 hours. The mix was filtered through Celite and concentrated to yield 3-[3-(4-Chloro-phenyl)-8-aza-bicyclo[3.2.1]oct-2-en-8-yl]-propylamine.

What is claimed is:

1. A compound of formula (I):

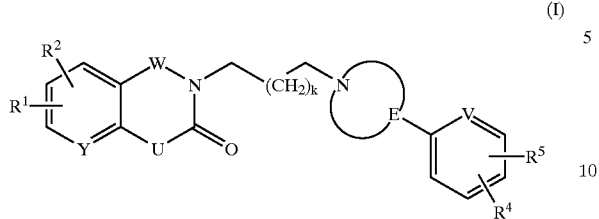

or pharmaceutically acceptable salts thereof, wherein the group

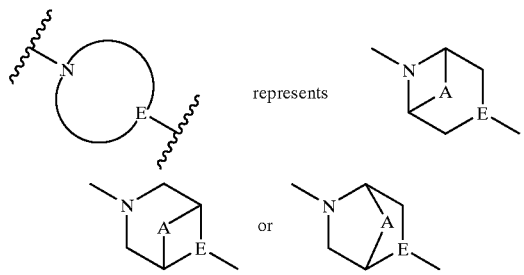 represents wherein, for each,

A is $(CH_2)_n$ where n is 1 or 2;
E is selected from the group consisting of N, CH, C—OH, C—CN, C—O—$(C_1-C_6)$alkyl, and C—$(C_1-C_6)$alkyl;
U is NH or $NR^3$, where $R^3$ is selected from the group consisting of $(C_1-C_6)$alkyl and C(=O)—$(C_1-C_6)$alkyl;
k is 1 or 2;
$R^1$ and $R^2$ are selected independently from H, $(C_1-C_6)$alkyl, halo, CN, nitro, $CF_3$, —NHC(O)$R^6$ and —$OR^7$, where $R^6$ and $R^7$ are selected independently from H, $(C_1-C_6)$alkyl, a 5- to 7-membered aryl ring, and a 5- to 7-membered heteroaryl ring; or $R^1$ and $R^2$, if on adjacent carbon atoms, together with the atoms to which they are attached, if adjacent, form a carbocyclic or heterocyclic five- or six-membered ring;
$R^4$ and $R^5$ are selected from H, $(C_1-C_6)$alkyl, halo, —$CF_3$, nitro, —CN, —NHC(=O)$R^6$, —$OR^7$, a 5- to 7-membered aryl ring, and a 5- to 7-membered heteroaryl ring; where $R^6$ and $R^7$ are as defined above;
V is CH, $CR^8$, or N, where $R^8$ is H, $(C_1-C_6)$alkyl, halo, —$CF_3$, nitro, —CN, —NHC(=O)$R^6$, —$OR^7$, a 5- to 7-membered aryl ring, or a 5- to 7-membered heteroaryl ring; wherein $R^6$ and $R^7$ are as defined above;
W is C(O); and
Y is CH, $CR^1$ or $CR^2$, where $R^1$ and $R^2$ are as defined above.

2. A compound according to claim 1 wherein

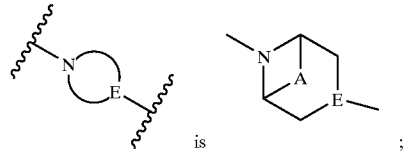 is ;

A is $(CH_2)_n$ where n is equal to 1 or 2;
W is C(=O);
Y is CH;
V is CH or N;
E is CH or N; and
U is NH.

3. A compound according to claim 1 wherein

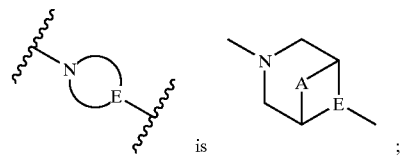 is ;

A is $(CH_2)_n$ where n is equal to 1 or 2;
W is C(=O);
Y is CH;
V is CH or N;
E is CH or N; and
U is NH.

4. A compound according to claim 1 wherein

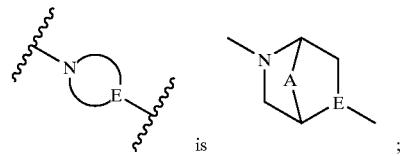 is ;

A is $(CH_2)_n$ where n is equal to 1 or 2;
W is C(=O);
Y is CH;
V is CH or N;
E is CH or N; and
U is NH.

5. A compound according to claim 1 wherein

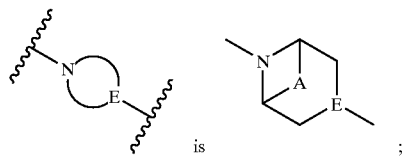 is ;

A is $(CH_2)_n$ where n is equal to 2;
W is C(=O);
Y is CH;
V is CH or N;
E is N
U is NH;
k is 1 or 2; and
$R^1$, $R^2$, $R^4$, and $R^5$ are independently chosen from the group consisting of hydrogen, halo, —$CF_3$, nitro, $(C_1-C_6)$alkyl, hydroxy and methoxy.

6. A compound according to claim 1 wherein

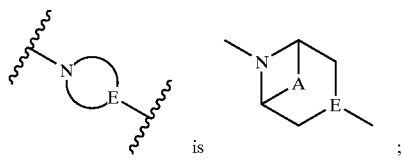

is

A is (CH$_2$)$_n$ where n is 2;
k is 1;
E is N;
W is C(=O);
Y is CH;
V is CH;
U is NH; and
R$^1$, R$^2$, R$^4$, and R$^5$ are independently chosen from the group consisting of hydrogen, hydroxy, methoxy, F, Cl, —CF$_3$, CN, nitro, (C$_1$–C$_6$)alkyl, a 5- to 7-membered aryl ring, and a 5- to 7-membered heteroaryl ring.

7. A compound according to claim 1 selected from the group consisting of
8-chloro-3-{3-[3-(4-chlorophenyl)-3,8-diazabicyclo[3.2.1]oct-8-yl]-propyl}-1H-quinazoline-2,4-dione;
8-chloro-3-[3-(8-p-tolyl-3,8-diazabicyclo[3.2.1]oct-3-yl]-propyl}-1H-quinazoline-2,4-dione;
8-chloro-3-{3-[8-(4-chloro-phenyl)-3,8-diazabicyclo[3.2.1]oct-3-yl]-propyl}-1H-quinazoline-2,4-dione;
3-{3-[3-(4-chloro-phenyl)-3,8-diazabicyclo[3.2.1]oct-8-yl]-propyl}-6-methyl-1H-quinazoline-2,4-dione;
3-{3-[3-(4-chloro-phenyl)-3,8-diazabicyclo[3.2.1]oct-8-yl]-propyl}-1H-quinazoline-2,4-dione;
3-[3-(3-p-tolyl-3,8-diazabicyclo[3.2.1]oct-8-yl)-propyl]-1H-quinazoline-2,4-dione;
3-{3-[3-(4-chloro-phenyl)-8-azabicyclo[3.2.1]oct-8-yl]-propyl}-1H-quinazoline-2,4-dione;
3-[3-(3-phenyl-8-azabicyclo[3.2.1]oct-8-yl)-propyl]-1H-quinazoline-2,4-dione;
3-[3-(3-p-tolyl-8-azabicyclo[3.2.1]oct-8-yl)-propyl]-1H-quinazoline-2,4-dione;
8-chloro-3-[3-(3-p-tolyl-3,8-diazabicyclo[3.2.1]oct-3-yl)-propyl]-1H-quinazoline-2,4-dione;
8-chloro-3-{3-[3-(2,4-dimethyl-phenyl)-3,8-diazabicyclo[3.2.1]oct-8-yl]-propyl}-1H-quinazoline-2,4-dione;
8-chloro-3-{3-[3-(3,4-dichloro-phenyl)-3,8-diazabicyclo[3.2.1]oct-8-yl]-propyl}-1H-quinazoline-2,4-dione;
3-{3-[3-(3,4-dichloro-phenyl)-3,8-diazabicyclo[3.2.1]oct-8-yl]-propyl}-1H-quinazoline-2,4-dione;
8-chloro-3-{3-[3-(4-fluoro-phenyl)-3,8-diazabicyclo[3.2.1]oct-8-yl]-propyl}-1H-quinazoline-2,4-dione;
3-{3-[3-(4-fluoro-phenyl)-3,8-diazabicyclo[3.2.1]oct-8-yl]-propyl}-1H-quinazoline-2,4-dione;
8-chloro-3-{3-[3-(4-trifluoromethyl-phenyl)-3,8-diazabicyclo[3.2.1]oct-8-yl]-propyl}-1H-quinazoline-2,4-dione;
3-{3-[3-(4-trifluoromethyl-phenyl)-3,8-diazabicyclo[3.2.1]oct-8-yl]-propyl}-1H-quinazoline-2,4-dione;
6,7-difluoro-3-[3-(3-p-tolyl-3,8-diazabicyclo[3.2.1]oct-8-yl)-propyl]-1H-quinazoline-2,4-dione;
6-fluoro-3-[3-(3-p-tolyl-3,8-diazabicyclo[3.2.1]oct-8-yl)-propyl]-1H-quinazoline-2,4-dione;
8-chloro-3-{4-[3-(4-chloro-phenyl)-3,8-diazabicyclo[3.2.1]oct-8-yl]-butyl}-1H-quinazoline-2,4-dione;
3-{4-[3-(4-chloro-phenyl)-3,8-diazabicyclo[3.2.1]oct-8-yl]-butyl}-6-methyl-1H-quinazoline-2,4-dione;
3-{4-[3-(4-chloro-phenyl)-3,8-diazabicyclo[3.2.1]oct-8-yl]-butyl}-1H-quinazoline-2,4dione;
8-chloro-3-{3-[8-(4-chloro-phenyl)-3,8-diazabicyclo[3.2.1]oct-3-yl]-propyl}-1H-quinazoline-2,4-dione;
8-chloro-3-{3-[5-(4-chloro-phenyl)-2,5-diazabicyclo[2.2.1]hept-2-yl]-propyl}-1H-quinazoline-2,4-dione;
8-chloro-3-{3-[5-(3-fluoro-phenyl)-2,5-diazabicyclo[2.2.1]hept-2-yl]-propyl}-1H-quinazoline-2,4-dione;
8-chloro-3-{3-[5-(4-fluoro-phenyl)-2,5-diazabicyclo[2.2.2]oct-2-yl]-propyl}-1H-quinazoline-2,4-dione;
8-chloro-3-{3-[5-(2,4-dimethyl-phenyl)-2,5-diazabicyclo[2.2.2]oct-2-yl]-propyl}-1H-quinazoline-2,4-dione;
8-chloro-3-{3-[5-(3,4-dichlorophenyl)-2,5-diazabicyclo[2.2.2]oct-2-yl]-propyl}-1H-quinazoline-2,4-dione;
3-{3-[5-(4-fluorophenyl)-2,5-diazabicyclo[2.2.2]oct-2-yl]-propyl}1H-quinazoline-2,4-dione;
and pharmaceutically acceptable salts thereof.

8. A pharmaceutical composition comprising a compound of claim 1 and a pharmaceutically acceptable carrier.

9. A process for preparing a compound of formula (I):

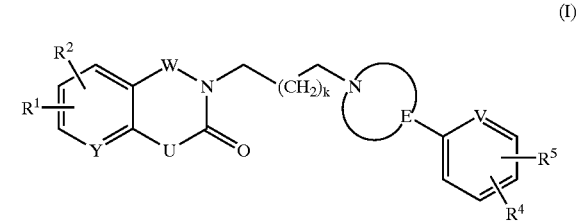

(I)

or pharmaceutically acceptable salts thereof, wherein the group

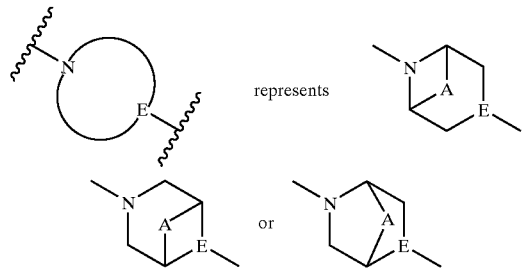

represents wherein, for each,
A is (CH$_2$)$_n$ where n is 1 or 2;
E is selected from the group consisting of N, CH, C—OH, C—CN, C—O—(C$_1$–C$_6$)alkyl, and C—(C$_1$–C$_6$)alkyl;
U is NH or NR$^3$, where R$^3$ is selected from the group consisting of (C$_1$–C$_6$)alkyl and C(=O)—(C$_1$–C$_6$)alkyl;
k is 1 or 2;
R$^1$ and R$^2$ are selected independently from H, (C$_1$–C$_6$) alkyl, halo, CN, nitro, CF$_3$, —NHC(O)R$^6$ and —OR$^7$, where R$^6$ and R$^7$ are selected independently from H, (C$_1$–C$_6$)alkyl, a 5- to 7-membered aryl ring, and a 5- to 7-membered heteroaryl ring; or R$^1$ and R$^2$, if on adjacent carbon atoms, together with the atoms to which they are attached, if adjacent, form a carbocyclic or heterocyclic five- or six-membered ring;
R$^4$ and R$^5$ are selected from H, (C$_1$–C$_6$)alkyl, halo, —CF$_3$, nitro, —CN, —NHC(=O)R$^6$, —OR$^7$, a 5- to 7-membered aryl ring, and a 5- to 7-membered heteroaryl ring; where R$^6$ and R$^7$ are as defined above;
V is CH, CR$^8$, or N, where R$^8$ is H, (C$_1$–C$_6$)alkyl, halo, —CF$_3$, nitro, —CN, —NHC(=O)R$^6$, —OR$^7$, a 5- to 7-membered aryl ring, or a 5- to 7-membered heteroaryl ring; wherein $R^6$ and $R^7$ are as defined above;
W is C(O); and
Y is CH, $CR^1$ or $CR^2$;
comprising the step of allowing a compound of formula (AII)

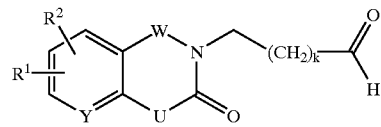

wherein
k is 1 or 2;
U is NH, or $NR^3$, where $R^3$ is selected from the group consisting of $(C_1-C_6)$alkyl, and $C(=O)-(C_1-C_6)$alkyl;
W is C(O);
Y is CH, $CR^1$ or $CR^2$, where $R^1$ and $R^2$ are as defined above
$R^1$ and $R^2$ are selected independently from H, $(C_1-C_6)$alkyl, halo, CN, nitro, $CF_3$, —NHC(O)$R^6$ and —$OR^7$, where $R^6$ and $R^7$ are selected independently from H, $(C_1-C_6)$alkyl, a 5- to 7-membered aryl ring, and a 5- to 7-membered heteroaryl ring, or
$R^1$ and $R^2$, together with the atoms to which they are attached, if adjacent to one another, form a carbocyclic or heterocyclic five- or six-membered ring;
to react with a compound of formula (BI)

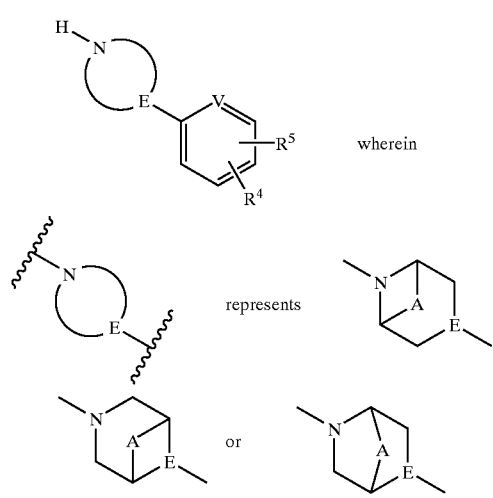

wherein, for each,
A is $(CH_2)_n$ where n is 1 or 2;
E is selected from the group consisting of N, CH, C—OH, C—CN, C—O—$(C_1-C_6)$alkyl, and C—$(C_1-C_6)$alkyl;
$R^4$ and $R^5$ are selected from H, $(C_1-C_6)$alkyl, halo, —$CF_3$, nitro, —CN, —NHC(=O)$R^6$, —$OR^7$, a 5- to 7-membered aryl ring, and a 5- to 7-membered heteroaryl ring; where $R^6$ and $R^7$ are as defined above;
V is CH, $CR^8$, or N, where $R^8$ is H, $(C_1-C_6)$alkyl, halo, —$CF_3$, nitro, —CN, —NHC(=O)$R^6$, —$OR^7$, a 5- to 7-membered aryl ring, or a 5- to 7-membered heteroaryl ring; wherein $R^6$ and $R^7$ are as defined above.

10. A process for the preparation of a compound of formula (I):

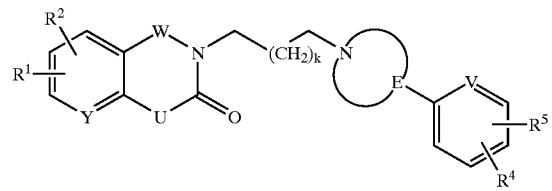

or pharmaceutically acceptable salts thereof, wherein the group

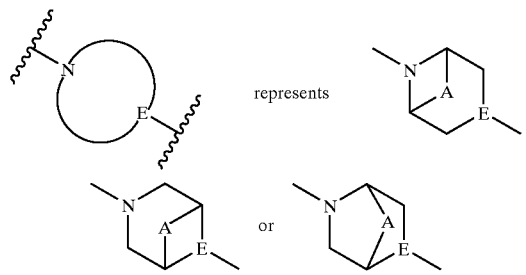

wherein, for each,
A is $(CH_2)_n$ where n is 1 or 2;
E is selected from the group consisting of N, CH, C—OH, C—CN, C—O—$(C_1-C_6)$alkyl, and C—$(C_1-C_6)$alkyl;
U is NH;
k is 1 or 2;
$R^1$ and $R^2$ are selected independently from H, $(C_1-C_6)$alkyl, halo, CN, nitro, $CF_3$, —NHC(O)$R^6$ and —$OR^7$, where $R^6$ and $R^7$ are selected independently from H, $(C_1-C_6)$alkyl, a 5- to 7-membered aryl ring, and a 5- to 7-membered heteroaryl ring; or $R^1$ and $R^2$, if on adjacent carbon atoms, together with the atoms to which they are attached, if adjacent, form a carbocyclic or heterocyclic five- or six-membered ring;
$R^4$ and $R^5$ are selected from H, $(C_1-C_6)$alkyl, halo, —$CF_3$, nitro, —CN, —NHC(=O)$R^6$, —$OR^7$, a 5- to 7-membered aryl ring, and a 5- to 7-membered heteroaryl ring; where $R^6$ and $R^7$ are as defined above;
V is CH, $CR^8$, or N, where $R^8$ is H, $(C_1-C_6)$alkyl, halo, —$CF_3$, nitro, —CN, —NHC(=O)$R^6$, —$OR^7$, a 5- to 7-membered aryl ring, or a 5- to 7-membered heteroaryl ring; wherein $R^6$ and $R^7$ are as defined above;
W is C(O); and
Y is CH, $CR^1$ or $CR^2$;
comprising the steps of
(a) allowing a compound of formula (AIII)

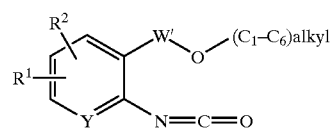

wherein W' is C(O); Y is CH, $CR^1$ or $CR^2$, and $R^1$ and $R^2$ are selected independently from H, $(C_1-C_6)$alkyl, halo, CN, nitro, $CF_3$, —NHC(O)$R^6$ and —$OR^7$, where $R^6$ and $R^7$ are selected independently from H, $(C_1-C_6)$alkyl, a 5- to 7-membered aryl ring and a 5- to 7-membered heteroaryl ring, or $R^1$ and $R^2$, together with the atoms to which they are attached, if adjacent, form a carbocyclic or heterocyclic five- or six-membered ring;

to react with a compound of formula (BII)

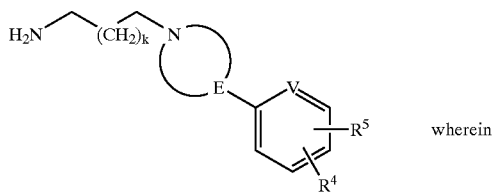

wherein

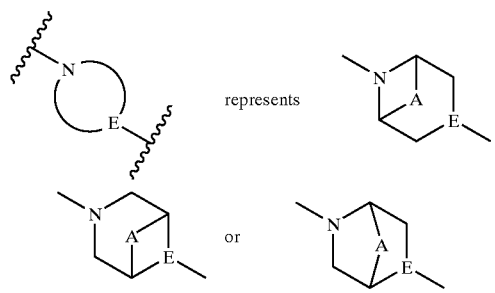

wherein

A is $(CH_2)_n$ where n is 1 or 2;
k is 1 or 2;
E is selected from the group consisting of N, CH, C—OH, C—CN, C—O—$(C_1-C_6)$alkyl, and C—$(C_1-C_6)$alkyl;
V is CH, $CR^3$, or N, where $R^3$ is as defined above; and
$R^4$ and $R^5$ are selected from H, $(C_1-C_6)$alkyl, halo, —$CF_3$, —CN, —NHC(=O)$R^6$, —$OR^7$, a 5- to 7-membered aryl ring, and a 5- to 7-membered heteroaryl ring, where $R^6$ and $R^7$ are as defined above;

to form a compound of formula (CI)

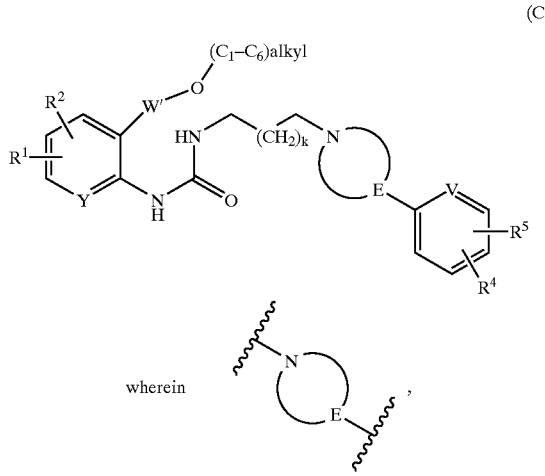

wherein k, $R^1$, $R^2$, Y, W', A, E, V, $R^4$, and $R^5$ are as defined above; and
(b) allowing the compound of formula (CI) to undergo a ring closure reaction.

11. A process for the preparation of compounds of formula (I):

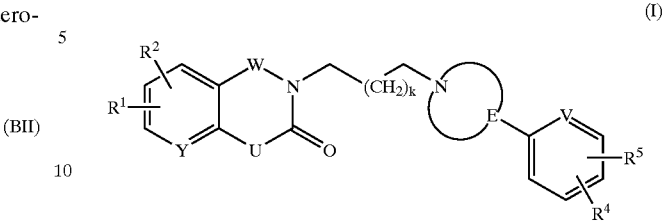

or pharmaceutically acceptable salts thereof, wherein the group

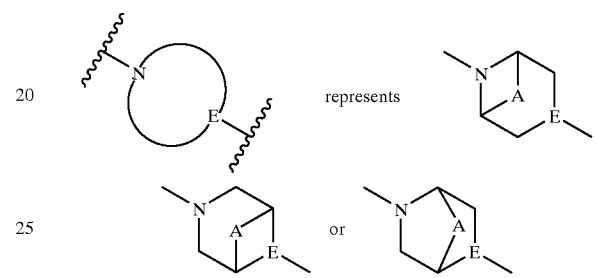

wherein, for each,

A is $(CH_2)_n$ where n is 1 or 2;
E is selected from the group consisting of N, CH, C—OH, C—CN, C—O—$(C_1-C_6)$alkyl, and C—$(C_1-C_6)$alkyl;
U is NH;
k is 1 or 2;
$R^1$ and $R^2$ are selected independently from H, $(C_1-C_6)$ alkyl, halo, CN, nitro, $CF_3$, —NHC(O)$R^6$ and —$OR^7$, where $R^6$ and $R^7$ are selected independently from H, $(C_1-C_6)$alkyl, a 5- to 7-membered aryl ring, and a 5- to 7-membered heteroaryl ring; or $R^1$ and $R^2$, if on adjacent carbon atoms, together with the atoms to which they are attached, if adjacent, form a carbocyclic or heterocyclic five- or six-membered ring;
$R^4$ and $R^5$ are selected from H, $(C_1-C_6)$alkyl, halo, —$CF_3$, nitro, —CN, —NHC(=O)$R^6$, —$OR^7$, a 5- to 7-membered aryl ring, and a 5- to 7-membered heteroaryl ring; where $R^6$ and $R^7$ are as defined above;
V is CH, $CR^8$, or N, where $R^8$ is H, $(C_1-C_6)$alkyl, halo, —$CF_3$, nitro, —CN, —NHC(=O)$R^6$, —$OR^7$, a 5- to 7-membered aryl ring, or a 5- to 7-membered heteroaryl ring; wherein $R^6$ and $R^7$ are as defined above;
W is C(O); and
Y is CH, $CR^1$ or $CR^2$;
comprising the steps of
(a) allowing a compound of formula (DIII)

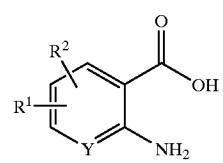

wherein Y, $R^1$ and $R^2$ are as defined above;

to react with a halo($C_3$–$C_4$)alkylisocyanate of the formula X—$(CH_2)_{k+2}$NCO, wherein k is 1 or 2, and X is halo, to form a compound of formula (GI)

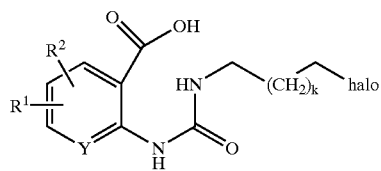
(GI)

wherein Y, $R^1$, $R^2$ and k are as defined above;
(b) allowing the compound of formula (GI) to undergo a double ring closure reaction to form a tricyclic compound of formula (FI)

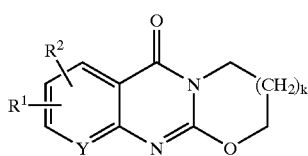
(FI)

wherein $R^1$, $R^2$ and Y are as defined above; and
(c) further permitting (FI) to react with a compound of formula (BI)

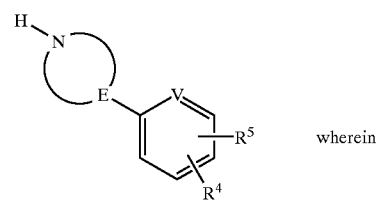
(BI)

wherein

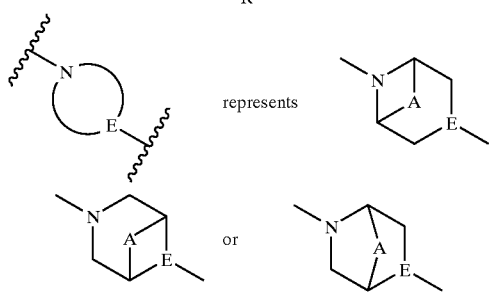 represents and E, V and $R^4$ and $R^5$ are as defined above, or a salt thereof.

12. A process according to any of claims 9, 10 or 11 wherein

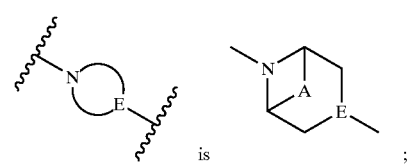 is ;

A is $(CH_2)_n$ where n is equal to 1 or 2;
W is C(=O);
Y is CH;
V is CH or N;
E is CH or N; and
U is NH.

13. A process according to any of claims 9, 10 or 11 wherein

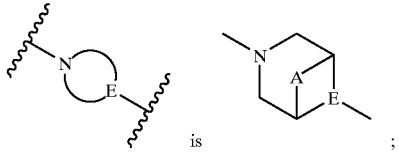 is ;

A is $(CH_2)_n$ where n is equal to 1 or 2;
W is C(=O);
Y is CH;
V is CH or N;
E is CH or N and
U is NH.

14. A process according to any one of claims 9, 10 or 11 wherein

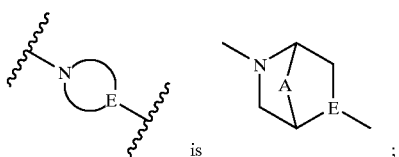 is ;

A is $(CH_2)_n$ where n is equal to 1 or 2;
W is C(=O);
Y is CH;
V is CH or N;
E is CH or N; and
U is NH.

15. A process according to any one of claims 9, 10 or 11 wherein

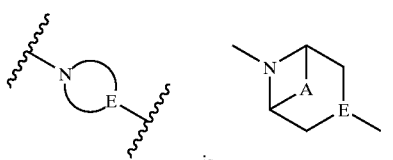 is ;

A is $(CH_2)_n$ where n is equal to 2;
W is C(=O);
Y is CH;
V is CH or N;
E is N;
U is NH;
k is 1 or 2; and
$R^1$, $R^2$, $R^4$, and $R^5$ are independently chosen from the group consisting of hydrogen, halo, —$CF_3$, nitro, ($C_1$–$C_6$)alkyl, hydroxy and methoxy.

16. A process according to any one of claims 9, 10 or 11 wherein

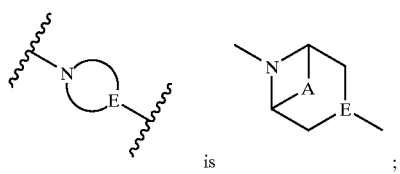

A is $(CH_2)_n$ where n is 2;
k is 1;
E is N;
W is C(=O);
Y is CH;
V is CH;
U is NH; and
$R^1$, $R^2$, $R^4$, and $R^5$ are independently chosen from the group consisting of hydrogen, hydroxy, methoxy, F, Cl, —$CF_3$, CN, nitro, $(C_1–C_6)$alkyl, a 5- to 7-membered aryl ring, and a 5- to 7-membered heteroaryl ring.

17. A method of treating anxiety or depression in a patient in need thereof comprising administering to the patient an effective amount of a compound of formula (I) according to claim 1.

* * * * *